Figure 1:
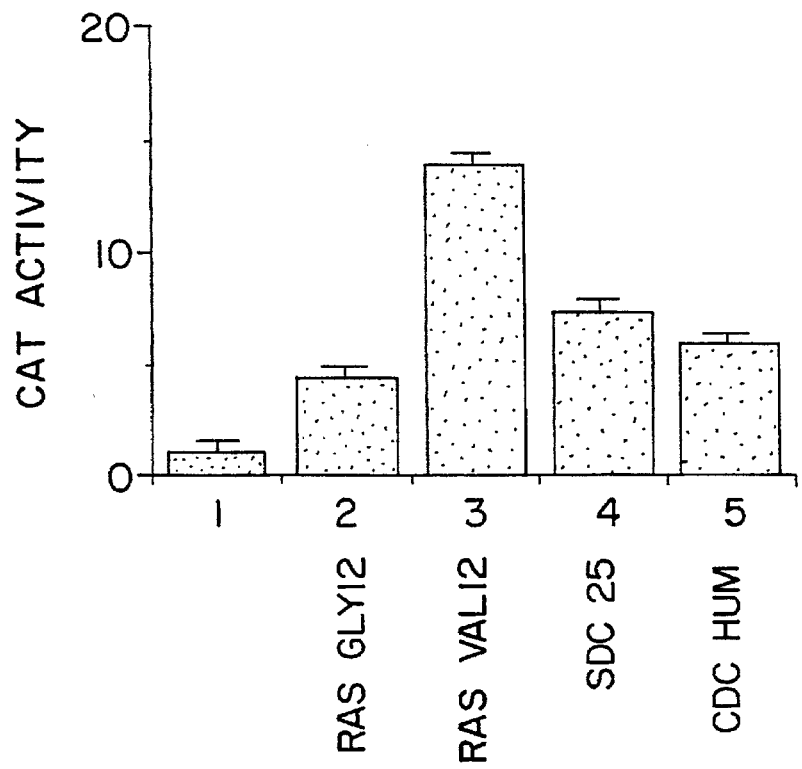

United States Patent [19]

Schweighoffer et al.

[11] Patent Number: 5,656,595
[45] Date of Patent: Aug. 12, 1997

[54] PEPTIDES HAVING GDP EXCHANGE FACTOR ACTIVITY, NUCLEIC ACID SEQUENCES CODING FOR THESE PEPTIDES, PREPARATION AND USE

[75] Inventors: Fabien Schweighoffer, Vincennes; Bruno Tocque, Paris, both of France

[73] Assignee: Rhone-Poulenc Rorer S.A., Antony, France

[21] Appl. No.: 318,831

[22] PCT Filed: Apr. 19, 1993

[86] PCT No.: PCT/FR93/00382

§ 371 Date: Oct. 19, 1994

§ 102(e) Date: Oct. 19, 1994

[87] PCT Pub. No.: WO93/21314

PCT Pub. Date: Oct. 28, 1993

[30] Foreign Application Priority Data

Apr. 21, 1992 [FR] France ................................. 92 04827

[51] Int. Cl.⁶ .......................... C12N 15/12; A61K 38/17; C07K 14/435

[52] U.S. Cl. .................. 514/12; 536/23.5; 530/350; 435/69.1

[58] Field of Search ...................... 530/350, 324–331; 356/23.14, 23.5, 24.34, 24.334; 435/6, 69.1, 69.7, 320.1, 240.2, 252.3; 514/2, 12

[56] References Cited

PUBLICATIONS

Bonfini, L. et al., *Science*, 255: 603–606, 1992 (Jan.).
Shou et al., *Nature*, 358: 351–4, 1992 (Jul.).
Martegani, E. et al., *EMBO J.*, 11(6): 2151–7, 1992 (Jun.).
Wei, W. et al., *PNAS*, 89: 7100–7104, Aug. 1992.

*Primary Examiner*—Marianne P. Allen
*Attorney, Agent, or Firm*—Julie K. Smith; Martin F. Savitzky

[57] ABSTRACT

The present invention relates to peptides capable of modulating the levels of GDP exchange on p21-GDP complexes, the nucleic acid sequences coding for said peptides, preparation thereof and pharmaceutical compositions containing them.

9 Claims, 2 Drawing Sheets

PEPTIDES HAVING GDP EXCHANGE FACTOR ACTIVITY, NUCLEIC ACID SEQUENCES CODING FOR THESE PEPTIDES, PREPARATION AND USE

The present invention relates to novel peptide and nucleotide sequences, and to their pharmaceutical use. More especially, the invention relates to peptides capable of modulating the levels of GDP exchange with p21-GDP complexes.

The products of ras genes, generally designated p21 proteins, perform a key role in the control of cell division in all eukaryotic organisms in which they have been investigated. Some specific modifications of these proteins cause them to lose their normal control and lead them to become oncogenic. Thus, a large number of human tumours have been associated with the presence of modified ras genes. Similarly, an overexpression of these p21 proteins can lead to a disturbance of cell proliferation. An understanding of the exact role of these p21 proteins in cells, their mode of functioning and their characteristics hence constitutes a major stake for an understanding of and therapeutic approach to carcinogenesis.

In vivo, the exact nature of the events responsible for the activation of p21 proteins is not yet known. It is known that they exert their functions by fluctuating between two confirmational states; an inactive form bound to GDP and an active form bound to GTP, but the factors effecting the transition between these two forms are not clearly identified. Recent studies report physiological situations during which the proportion of ras proteins bound to GTP increases in the cell. These situations comprise the activation of T lymphocytes and the stimulation of 3T3 fibroblasts by growth factors including EGF and PDGF (Downward et al., Nature 346 (1990) 719; Gibbs et al., J. Biol. Chem. 265 (1990) 20437). The increase in the proportion of p21-GTP may be at least partially explained by the action of a protein performing a role analogous to that of a receptor of the G proteins of transduction. In this connection, some proteins capable of promoting the exchange of GDP with p21 proteins have been identified, from ox brain [West et al., FEBS Lett. 259 (1990) 245] and rat brain [Wolfman and Macara, Science 248 (1990) 67]. The differing cellular localization of these under which they were obtained suggests that they are different proteins. They are as active on normal ras proteins as on those which are oncogenic. These activities are grouped together under the term GEF: Guanidine nucleotide Exchange Factor, or GRF.

In *Saccharomyces cerevisiae* yeast, GRF activity has been attributed to the product of the CDC25 gene [Camonis et al., EMBO J. 5 (1986) 375], and studies have been carried out in order to understand the signalling pathway involving the product of the CDC25, RAS1 and RAS2 genes on the one hand and adenylate cyclase on the other hand in *Saccharomyces cerevisiae* yeast. In particular, many studies have focused on characterization of the product of the CDC25 gene, which was the least known element of this chain. The product of the CDC25 gene constitutes the element furthest upstream in the cascade of reactions leading to the activation of p21 in yeast. The work carried out in this field has contributed to demonstrating that the product of this gene must act as a GDP→GTP exchange factor for activating ras proteins. A second gene of *S. cerevisiae* yeast, SDC25, structurally very closely related to CDC25, has been isolated and characterized. The active domain of SDC25 seems to be an exchange factor capable of acting in vitro and in vivo on ras proteins. This domain constitutes the first molecular constituent described which is endowed with this activity.

Very recently, a protein of the GRF type has also been demonstrated in mice [Vanoni and Martegani, J. Cell. Bioch. Suppl. 16B (1992) 220].

However, to date, no GRF activity has been isolated and characterized in man. The present invention is specifically the outcome of the demonstration by the Applicant of the existence of a human GDP exchange factor. The present invention is, more especially, the outcome of the identification, isolation and characterization of peptides and nucleotide sequences of human origin, designated hGRF and hSOS, capable of modulating the state of activation of p21 proteins.

A first aspect of the hence invention consists of peptides which can be used pharmaceutically. More especially, a subject of the invention lies in peptides capable of modulating the levels of exchange of GDP with p21-GDP complexes. It is understood that p21 denotes any expression product of a normal or oncogenic ras gene.

More especially, the peptides of the invention are chosen from all or part of the sequences SEQ ID no. 2, 3, 4, 6 or 8, or of a derivative of these sequences.

For the purposes of the present invention, the term derivative denotes any molecule obtained by modification, of a genetic and/or chemical nature, of these sequences and which retains the desired activity. Modification of a genetic and/or chemical nature should be understood to mean any mutation, substitution, deletion, addition and/or modification of one or more residues. Such derivatives may be generated for different purposes, such as, in particular, that of increasing the affinity of the peptide for its interaction site, that of improving its levels of production, that of increasing its resistance to proteases, that of increasing its therapeutic efficacy or of reducing its side effects, or that of endowing it with novel pharmacokinetic and/or biological properties.

In a particular embodiment of the invention, the peptides of the invention are peptides capable of stimulating the exchange of GDP with the p21-GDP complex.

In another particular embodiment of the invention, the peptides of the invention are peptides capable of slowing down or inhibiting the exchange of GDP with the p21-GDP complex. Such peptides are preferably peptides capable of antagonizing the interaction of GDP exchange factor with the p21-GDP complex. Hence they can be fragments of the sequences mentioned above or of derivatives of these sequences. Such fragments may be generated in different ways. In particular, they may be synthesized chemically on the basis of the sequences given in the present application, using the peptide synthesizers known to a person skilled in the art. They may also be synthesized genetically, by expression in a cell host of a nucleotide sequence coding for the desired peptide. In this case, the nucleotide sequence may be prepared chemically using an oligonucleotide synthesizer, on the basis of the peptide sequence given in the present application and the genetic code. The nucleotide sequence may also be prepared from the sequences given in the present application (SEQ ID no. 1, 5 and 7), by enzymatic cleavages, ligation, cloning, and the like, according to the techniques known to a person skilled in the art, or by the screening of DNA libraries with probes produced on the basis of these sequences. Moreover, the peptides of the invention, capable of slowing down or inhibiting the exchange of GDP with the p21-GDP complex, can also be peptides having a sequence corresponding to the site of interaction of the exchange factor with the p21-GDP complex.

Another subject of the invention lies in polyclonal or monoclonal antibodies or antibody fragments directed against a peptide as is defined above. Such antibodies may be generated by methods known to a person skilled in the art, in the light of the teachings given in the present application. In particular, these antibodies may be prepared by immunization of an animal against a peptide of the invention, withdrawal of blood and isolation of the antibodies. These antibodies may also be generated by the preparation of hybridomas according to the techniques known to a person skilled in the art.

More preferably, the antibodies or antibody fragments of the invention possess the capacity to inhibit at least partially the interaction of the exchange factor with the p21-GDP complex. They may thus be used to regulate the state of activation of the product of ras genes.

Moreover, these antibodies may also be used to detect and/or assay human GDP exchange factor in biological samples, and consequently to provide information about the state of activation of the product of ras genes.

The present invention hence makes it possible to generate peptides derived from the sequences SEQ ID no. 2–4, 6 and 8, as well as antibodies directed against these peptides, possessing advantageous biological properties with a view to pharmaceutical use. The biological activity of the different peptides and antibodies of the invention with respect to GDP exchange may be evaluated in different way, as illustrated in the examples.

The invention also provides compounds which are non-peptide or not exclusively peptide in nature and which can be used pharmaceutically. It is, in effect, possible, starting from the active proteinaceous units described in the present application, to produce molecules which inhibit the ras protein-dependant signalling pathway which are not exclusively peptide in nature and are compatible with pharmaceutical use. In this connection, the invention relates to the use of a polypeptide of the invention as is described above for the preparation of molecules which are non-peptide or not exclusively peptide in nature and are pharmacologically active on the levels of GDP exchange, by determination of the structural elements of this polypeptide which are important for its activity and reproduction of these elements by structures which are non-peptide or not exclusively peptide in nature. The subject of the invention is also pharmaceutical compositions comprising one or more molecules thus prepared.

The subject of the present invention is also any nucleic acid sequence coding for a polypeptide as is defined above. More preferably, the sequence in question is chosen from:

(a) all or part of the sequences SEQ ID no. 1, 5 or 7 or of their complementary strand, (b) any sequence hybridizing with a sequence (a) and coding for a polypeptide according to the invention, and (c) the sequences derived from the sequences (a) and (b) as a result of the degeneracy of the genetic code.

The different nucleotide sequences of the invention can be of artificial origin or otherwise. They can be genomic, cDNA, RNA sequences, hybrid sequences or synthetic or semi-synthetic sequences. These sequences may be obtained, for example, by the screening of DNA libraries (cDNA library, genomic DNA library) by means of probes produced on the basis of the sequences SEQ ID no. 1, 5 or 7. Such libraries may be prepared from cells of different origins by standard techniques of molecular biology known to a person skilled in the art. The nucleotide sequences of the invention may also be prepared by chemical synthesis, in particular according to the phosphoramidite method, or alternatively by mixed methods including the chemical or enzymatic modification of sequences obtained by the screening of libraries.

These nucleotide sequences according to the invention can be used in the pharmaceutical field, such use either being for the in vitro production of the peptides of the invention, or being for the production of anti-sense sequences or for the production of the peptides of the invention in the context of a gene therapy, or alternatively being for the detection and diagnosis, by hybridization experiments, of the expression or of an overexpression of an amplified, mutated or rearranged GDP exchange factor in biological samples, or for the isolation of homologous sequences from other cell sources.

For the production of the peptides of the invention, the nucleic acid sequences defined above are generally placed under the control of signals permitting their expression in a cell host. The choice of these signals (promoters, terminators, secretion leader sequence, and the like) can vary in accordance with the cell host used. Preferably, these nucleotide sequences of the invention form part of a vector, which can be autonomously replicating or integrative. More especially, autonomously replicating vectors may be prepared using sequences displaying autonomous replication in the chosen host. Integrative vectors, for their part, may be prepared, for example, using sequences homologous to certain regions of the host's genome, permitting integration of the vector by homologous recombination.

The cell hosts which can be used for the production of the peptides of the invention are equally well eukaryotic or prokaryotic hosts. Among eukaryotic hosts which are suitable, animal cells, yeasts or fungi may be mentioned. In particular, as regards yeasts, yeasts of the genus Saccharomyces, Kluyveromyces, Pichia, Schwanniomyces or Hansenula may be mentioned. As regards animal cells, COS, CHO, C127 cells, and the like, may be mentioned. Among fungi, Aspergillus ssp. or Trichoderma ssp. may be mentioned more especially. As prokaryotic hosts, it is preferable to use the following bacteria, E. coli, Bacillus or Streptomyces.

The nucleic acid sequences according to the invention may also be used for the production of anti-sense oligonucleotides or of genetic anti-sense sequences which can be used as pharmaceutical agents. Inhibition of the expression of certain oncogenes by anti-sense sequences has proved to be a useful strategy in understanding the role of these oncogenes, and an especially promising approach in the production of an anticancer treatment. Anti-sense sequences are small-sized oligonucleotides which is complementary to the coding strand of a given gene and which, as a result, are capable of hybridizing specifically with the transcribed mRNA, inhibiting its translation into protein. The subject of the invention is thus anti-sense sequences capable of at least partially inhibiting the production of peptides stimulating the exchange of GDP with p21-GDP complexes. Such sequences can consist of all or part of the nucleic acid sequences defined above. They are generally sequences or fragments of sequences complementary to sequences coding for peptides stimulating GDP exchange. Such oligonucleotides may be obtained from the sequences SEQ ID no. 1, 5 or 7, by fragmentation, and the like, or by chemical synthesis. Such sequences may be used in the context of gene therapies, for the transfer and in vivo expression of anti-sense sequences or of peptides capable of modulating the levels of exchanges of GDP with ras proteins. In this connection, the sequences may be incorporated in vectors, in particular of viral origin.

The invention also relates, as nucleotide sequences, to nucleotide probes, synthetic or otherwise, capable of hybridizing with the nucleotide sequences defined above which code for a peptide of the invention, or with the corresponding mRNA. Such probes may be used in vitro as a diagnostic tool, for detection of the expression of GDP exchange factor, or alternatively for the demonstration of genetic abnormalities (incorrect splicing, polymorphism, point mutations, and the like). Such probes must be labelled beforehand, and different techniques for this purpose are known to a person skilled in the art. The hybridization conditions under which these probes can be used are the normal conditions of stringency (see, in particular, the general cloning techniques below as well as the examples). These probes may also be used for the demonstration and isolation of homologous nucleic acid sequences coding for a peptide of the invention, from other cell sources, as illustrated in the examples.

The subject of the invention is also any pharmaceutical composition comprising as active principle at least one peptide as is defined above.

Its subject is also any pharmaceutical composition comprising as active principle at least one antibody and/or antibody fragment as is defined above, as well as any pharmaceutical composition comprising as active principle at least one nucleotide sequence as is defined above.

Moreover, its subject is also pharmaceutical compositions in which the peptides, antibodies and nucleotide sequence defined above are combined with one another or with other active principles.

The pharmaceutical compositions according to the invention may be used to modulate the activation of p21 proteins and, as a result, to modulate the proliferation of certain cell types. More especially, these pharmaceutical compositions are intended for the treatment of cancers. Many cancers have, in effect, been associated with the presence of oncogenic ras proteins. Among cancers most often containing mutated ras genes, there may be mentioned, in particular, adenocarcinomas of the pancreas, 90% of which have a Ki-ras oncogene mutated on the twelfth codon [Almoguera et al., Cell 53 (1988) 549], adenocarcinomas of the colon and cancers of the thyroid (50%), or carcinomas of the lung and myeloid leukaemias [30%, Bos, J. L. Cancer Res. 49 (1989) 4682].

The subject of the invention is also the use of the molecules described above for modulating the activity of p21 proteins. In particular, the invention relates to the use of these molecules for at least partially inhibiting the activation of p21 proteins.

The invention also provides a method for detection of the expression and/or of an overexpression of a ras gene in a biological sample. Such a method comprises, for example, bringing such a sample into contact with an antibody or antibody fragment according to the invention, visualization of the antigen-antibody complexes and comparison of the results obtained with a standard sample. In such a method, the antibody may be in suspension or immobilized beforehand on a support. This method can also comprise bringing the sample into contact with a nucleotide probe according to the invention, demonstration of hybrids obtained and comparison with those obtained in the case of a standard sample.

The present invention may be used in the therapeutic field: since the peptides, antibodies and nucleotide sequences of the invention are capable of modulating the activity of ras genes, they make it possible, in effect, to intervene in the process of development of cancers. As illustrated in the examples, the nucleotide sequences of the invention make it possible, in particular, to express peptides capable of complementing the temperature sensitivity of yeasts carrying a cdc25 mutation. They also make it possible to express peptides capable of suppressing a RAS2ts dominant mutation, demonstrating a competition with the normal expression product of the CDC25 gene for interaction with the p21 proteins. The invention may also be used in the field of diagnosis and typing of cancers: the antibodies and nucleotide probes of the invention make possible, in effect, the identification of cancers in which a ras gene is involved, as well as the diagnosis of cancers associated with the overexpression of a normal or oncogenic ras gene.

Other advantages of the present invention will become apparent on reading the examples which follow, which are to be considered as illustrative and non-limiting.

LEGEND TO THE FIGURES

FIG. 1: Trans-activation test: This figure shows as ordinates the levels of CAT activity (% relative to background) of recombinant CHO strains, according to the cDNA sequence used for the transformation.

Figure 2:
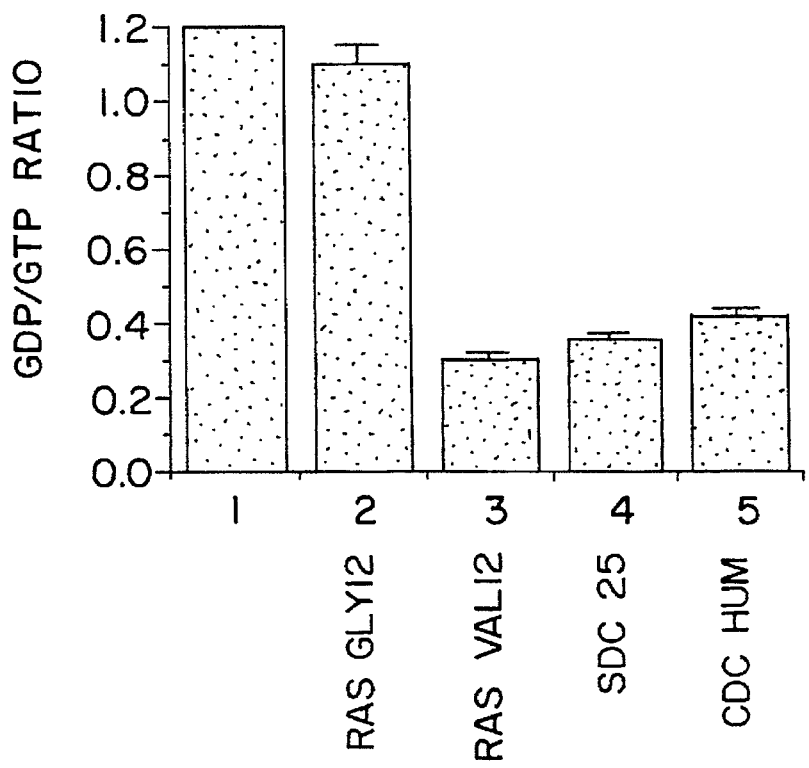

FIG. 2: Test of GTP exchange activity: This figure shows as ordinates the ratio of the p21-GDP/p21-GTP forms of recombinant CHO strains, according to the cDNA sequence used for the transformation.

Figure 3:
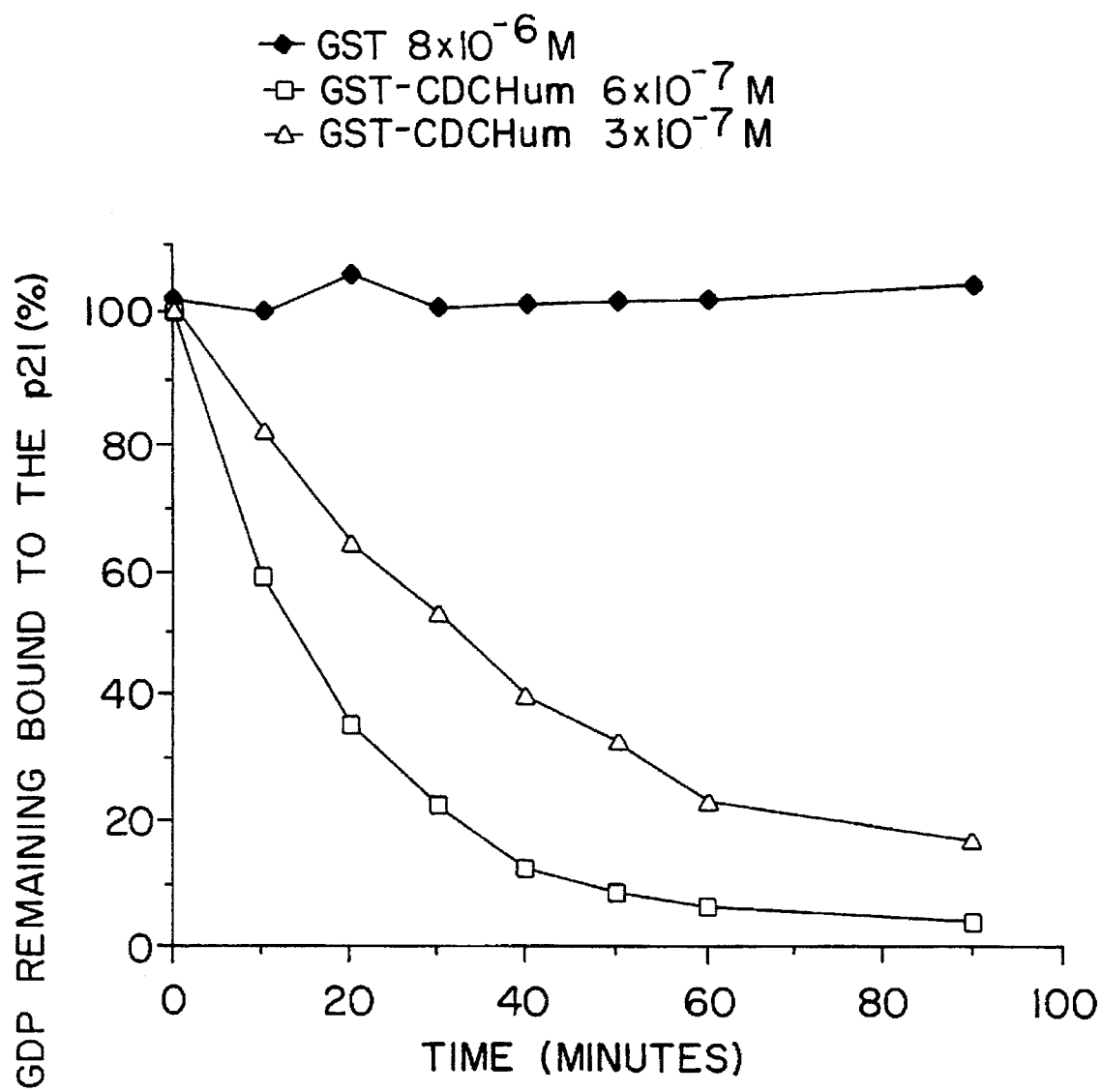

FIG. 3: Test of GDP exchange activity in vitro: This figure shows, in terms of time and for 2 concentrations of a peptide of the invention, the decrease in the proportion of GDP remaining bound to the p21 protein.

GENERAL CLONING TECHNIQUES

The methods traditionally used in molecular biology, such as preparative extractions of plasmid DNA, centrifugation of plasmid DNA in a caesium chloride gradient, agarose or acrylamide gel electrophoresis, purification of DNA fragments by electroelution, protein extractions with phenol or phenol/chloroform, ethanol or isopropanol precipitation of DNA in a saline medium, transformation in *Escherichia coli*, and the like, are well known to a person skilled in the art and are amply described in the literature [Maniatis T. et al., "Molecular Cloning, a Laboratory Manual", Cold Spring Harbor Laboratory, Cold Spring Harbor, N.Y., 1982; Ausubel F. M. et al. (eds), "Current Protocols in Molecular Biology", John Wiley and Sons, New York 1987].

Restriction enzymes were supplied by New England Biolabs (Biolabs), Bethesda Research Laboratories (BRL) or, Amersham, and are used according to the suppliers' recommendations.

Plasmids of the pBR322, pUC, λgt11 and pGEX 2T type and phages of the M13 series are of commercial origin.

For ligation, the DNA fragments are separated according to size by agarose or acrylamide gel electrophoresis, extracted with phenol or with a phenol/chloroform mixture, precipitated with ethanol and then incubated in the presence of phage T4 DNA ligase (Biolabs) according to the supplier's recommendations.

The filling of 5' protruding ends is performed with the Klenow fragment of *E. coli* DNA polymerase I (Biolabs) according to the supplier's specifications. The destruction of 3' protruding ends is performed in the presence of phage T4 DNA polymerase (Biolabs) used according to the manufacturer's recommendations. The destruction of 5' protruding ends is performed by a controlled treatment with S1 nuclease.

Mutagenesis directed in vitro by synthetic oligodeoxynucleotides is performed according to the method developed by Taylor et al. [Nucleic Acids Res.13 (1985) 8749–8764] using the kit distributed by Amersham.

The enzymatic amplification of DNA fragments by the so-called PCR [Polymerase-catalyzed Chain Reaction, Saiki R. K. et al., Science 230 (1985) 1350–1354; Mullis K. B. and Faloona F. A., Meth. Enzym. 155 (1987) 335–350] technique is performed using a "DNA thermal cycler" (Perkin Elmer Cetus) according to the manufacturer's specifications.

Verification of the nucleotide sequences is performed by the method developed by Sanger et al. [Proc. Natl. Acad. Sci. USA, 74 (1977) 5463–5467] using the kit distributed by Amersham.

For the hybridization experiments, the normal conditions of stringency are generally as follows: hybridization: 3× SCC in the presence of 5× Denhart's at 65° C.; washing: 0.5× SSC at 65° C.

1. Isolation of the human GDP exchange factor (hGRF) gene $5 \times 10^5$ phages of a human brain library constructed in the vector λgt11 [Skolnik et al., Cell 65 (1991) 83] were screened according to the techniques described by Sambrook, Fritsch and Maniatis (Molecular cloning; Cold Spring Harbor Laboratory Press; 1989).

The probe used for the screening of this library is a $^{32}$P-labelled 137-base pair human cDNA fragment. This probe was prepared by PCR on the total DNA of the abovementioned library using the following degenerate oligonucleotides as primers:

| -ATC | CGT | CAG | GTA | CAT | CCC | CAG | GTA | TGG | CAC | ACA |
|------|-----|-----|-----|-----|-----|-----|-----|-----|-----|-----|
|      | T   | T   |     |     | T   | T   |     | T   | T   |     |
|      | A   | A   |     |     | A   | A   |     |     | G   | A   |
|      |     | G   |     |     | G   |     |     |     | G   |     | for the oligonucleotide of the 3' end of the fragment (SEQ ID no. 11), and

| -GCA | ATT | TTT | CGG | CTT | AAG | AAG | ACT | TGG |
|------|-----|-----|-----|-----|-----|-----|-----|-----|
| T    | C   | C   | A   | C   | A   | A   | C   |     |
| C    | A   |     | T   | G   |     |     | A   |     |
| G    |     |     | C   | A   |     |     | G   |     | for the oligonucleotide of the 5' end of the fragment (SEQ ID no. 12).

The probe was labelled with $^{32}$P by random priming according to the technique of Feinberg and Vogelstein [Anal. Biochem. 137 (1984) 266], and the PCR reaction was conducted at approximately 40° C. under the conditions described in the general cloning techniques.

Among the different positive clones obtained by hybridization with this probe, one comprises the whole of an open reading frame which carries the exchange activity with respect to Ha-Ras.

This λgt11 clone contains a 3-kb cDNA which has been introduced in the form of an EcoRI fragment at the corresponding site of an M13mp18 vector. This cDNA was then sequenced using commercial "reverse" and "–20" primers and also using specific oligonucleotides according to the Sanger technique (see general cloning techniques).

The nucleotide sequence of the human GDP exchange factor gene carried by the fragment thereby obtained is presented in the sequence SEQ ID no. 1, together with the deduced peptide sequences (SEQ ID no. 2, 3 and 4).

2. Preparation of subfragments

Different derivatives or fragments of the gene thereby obtained may be prepared and used, in particular for the expression of peptides of the invention. In particular, the following fragments were prepared by enzymatic cleavage, and separated by electroelution:

a PstI-EcoRI fragment comprising a portion of the exchange factor coding region (936 up to the stop codon) as well as the 3' non-coding region of the fragment, an EcoNI-EcoRI fragment comprising a portion of the exchange factor coding region (910 up to the stop codon) as well as the 3' non-coding region of the fragment, an EagI-EcoRI fragment comprising a portion of the exchange factor coding region (up to the stop codon) as well as the 3' non-coding region of the fragment, a BalI-EcoRI fragment comprising a portion of the exchange factor coding region (up to the stop codon) as well as the 3' non-coding region of the fragment, and an NaeI-EcoRI fragment comprising a portion of the exchange factor coding region (up to the stop codon) as well as the 3' non-coding region of the fragment, It is understood that the 3' non-coding region carried by these fragments is of secondary importance and that it may be removed, either by digestion by means of a nuclease, or by cleavage with an enzyme having a site close to the stop codon, such as, in particular, SmaI, the site for which is localized approximately 30 bp after the stop codon.

It is also understood that other fragments may be prepared, such as, in particular, fragments not containing the region coding for the entire C-terminal portion, as well as derivatives of these fragments, obtained by mutation, substitution, addition or modification of a chemical and/or genetic nature.

3. Biological characterization

The functionalities of the peptides according to the invention were tested:

in mammalian cells, in *Saccharomyces cerevisiae* yeast, or alternatively in vitro on the recombinant Ha-Ras protein.

3.1. For the functional evaluation in mammalian cells, the DNA sequences coding for peptides of the invention, such as for example, those described in Example 2, may be placed under the control of the SV40 early promoter in the vector pCym1 described by Camonis et al. [Gene 86 (1990) 263].

In this example, the PstI-EcoRI and EcoNI-EcoRI fragments described in Example 2 were inserted into this vector.

The vectors thereby obtained were tested by transient transfection into CHO cells according to the protocol described by Rey et al. [Oncogene 6 (1991) 347].

Two criteria of functionality were studied in this way:

the capacity of the vectors to trans-activate a promoter governing the expression of a reporter gene, which is, in this instance, the bacterial gene coding for chloramphenicol acetyltransferase (CAT gene), their capacity to promote the loading with GTP of the Ras protein of transfected CHO cells.

a) For the trans-activation tests, CHO cells at 50% confluence were transfected (see, for example, the protocol described by Schweighoffer et al., Science, In Press), on the one hand with 0.5 µg of a vector carrying the CAT gene under the control of a synthetic promoter composed of the murine promoter of the thymidine kinase gene and 4 PEA1 repeat elements derived from the polyoma enhancer [Wasylyk et al., EMBO J. 7 (1988) 2475), and on the other hand with 4.5 μg of an expression vector carrying, under the control of the SV40 early promoter, no coding cDNA (lane 1), cDNA of normal Ha-Ras (lane 2), cDNA of Ha-Ras activated at position 12 (Val 12) (lane 3), the 3' end of SDC25 cDNA, described by Rey et al. cited above (lane 4), and cDNA coding for a peptide according to the invention, described above (lane 5).

The results are presented in FIG. 1. With lane 1 corresponding to the baseline activation, lane 5 (obtained for the PstI-EcoRI fragment: CDC hum.) shows that the expression of a peptide of the invention permits trans-activation of the synthetic promoter studied.

The same qualitative result was obtained for the other fragments studied.

b) So as to verify that this trans-activation does indeed involve a loading of the ras proteins of CHO cells with nucleotides, the same transient transfections were carried out with $^{32}$P-labelled orthophosphate being added to the culture medium.

This labelling protocol, as well as that for the immunoprecipitation of cellular ras proteins, is described by Rey et al. cited above. The results obtained are presented in FIG. 2. They show that the peptides of the invention are capable of modulating the levels of exchange of GDP with ras proteins, since some of them (peptide CDC Hum. expressed by the PstI-EcoRI fragment described above) are capable of promoting the loading with GTP of the ras proteins of CHO cells immunoprecipitated with Y 13-259 antibody.

3.2. The peptides of the invention were also tested functionally in S. cerevisiae cdc25⁻ yeast. To this end, the vectors described above (3.1.), which are shuttle vectors, were introduced into the yeast strain OL97-1-11B [Camonis and Jacquet, Mol. Cell. Biol. 8 (1988) 2980]. The results obtained show that the cDNA fragments according to the invention code for peptides which are capable of complementing the lack of growth of this strain at 36° C. These results thus show that these fragments code for peptides which are functional in vivo in S. cerevisiae.

3.3. The capacity of the DNA sequences of the invention to code for peptides capable of promoting the exchange of GDP with purified Ha-Ras proteins was also demonstrated in vitro according to the protocol described by Rey et al. Mol. Cell. Biol. 9 (1989) 3904].

To this end, the sequences of the invention are expressed in E. coli strain TG1 in the form of fusion proteins with glutathione S-transferase (GST) according to the technique described by Smith and Johnson [Gene 67 (1988) 31]. To this end, the different DNA fragments described in 3.1. above were cloned, in the form of SmaI-EcoRI fragments, into the vector pGEX 2T (Pharmacia), at the 3' end of, and in frame with, a cDNA coding for GST. The SmaI-EcoRI fragments are obtained by adding an adapter by means of a ligase. The vectors thereby obtained are then used to transform E. coli strain TG1. The cells thus transformed are precultured overnight at 37° C., diluted to ¹/₁₀ in LB medium, added of IPTG to induce expression (2 hours, 25° C.) and then cultured for approximately 21 hours at 25° C. The cells are then lysed, and the fusion proteins produced are purified by affinity on an agarose-GSH column. To this end, the bacterial lysate is incubated in the presence of the gel (prepared and equilibrated with the lysis buffer) for 15 minutes at 4° C. After three washes with a Tris-HCl buffer, pH 7.4, the proteins are eluted in the presence of a Tris-HCl buffer, pH 7.7, containing an excess of GSH. The supernatant is harvested and centrifuged.

The GDP exchange activity of the peptides of the invention with respect to purified Ha-Ras proteins was then demonstrated in vitro according to the protocol described by Rey et al. (Mol. Cell. Biol. cited above). The results obtained are presented in FIG. 3. They show, in particular, that the peptide of the invention corresponding to the CDC hum sequence, expressed by the PstI-EcoRI fragment described above, stimulates GDP exchange.

4. Demonstration of homologous sequences

Nucleic acid sequences homologous to that presented in FIG. 1 were demonstrated by two different strategies:

by PCR, under the conditions described in the general cloning techniques, on cDNAs neosynthesized from placental mRNA, using as primers degenerate oligonucleotides chosen to cover sequences which are conserved between the sequence SEQ ID no. 1 and the sequence of the SOS protein [Bonfini et al., Science 255 (1992) 603].

By screening a placental cDNA library using a probe consisting of the whole of the sequence SEQ ID no. 1 labelled with $^{32}$P. This screening was carried out under conditions of low stringency: hybridization at 50° C. in 5× SSC, 5× Denhart's medium; followed by washing at 50° C. in 2× SSC medium.

These two strategies enabled sequences homologous to the sequence SEQ ID no. 1 to be revealed. These sequences may be readily isolated and characterized. They constitute nucleic acid sequences for the purposes of the present invention when they code (or their fragments or derivatives) for peptides capable of modulating the levels of exchanges of GDP with p21-GDP complexes.

In particular, this strategy made it possible to identify, from placental mRNA and using the oligonucleotides oligo 2449 (SEQ ID no. 9) and oligo 2451 (SEQ ID no. 10), 2 cDNAs coding for factors designated hSOS1 and hSOS2, the partial sequences of which are shown in SEQ ID no. 5 and SEQ ID no. 7, respectively. The mRNAs corresponding to these factors are present in all tissues in which they have been looked for, in contrast to the factor described in Example 1 which appears to be localized only in the brain. The chromosomal localization of these genes was performed, and gave the following results:

h-GRF:15q2.4.

h-SOS1:4q2.1.

h-SOS2:14q2.2.

5. Testing for exchange factors of the h-GRF type in other tissues

An anti-h-GRF antibody was prepared in rabbits by immunization with an antigen corresponding to the fragment of 280 amino acids localized between residues 211 and 489 of the h-GRF factor presented in SEQ ID no. 4.

These antibodies enabled proteins of apparent molecular weights 30, 55, 75, 95 and 140 kDa to be detected, by ELISA, in human cortex and brain precursor cells. The diversity of molecular weights suggests the presence of multiple cDNAs. Preincubation of the anti-h-GRF antibody with h-GRF abolishes the detection of the proteins identified, thereby demonstrating the specificity of the signal.

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
( A ) LENGTH: 2652 base pairs
( B ) TYPE: nucleic acid
( C ) STRANDEDNESS: double
( D ) TOPOLOGY: linear ( i i ) MOLECULE TYPE: cDNA ( i i i ) HYPOTHETICAL: NO ( i i i ) ANTI-SENSE: NO ( i x ) FEATURE:
( A ) NAME/KEY: CDS
( B ) LOCATION: 1..2445

( i x ) FEATURE:
( A ) NAME/KEY: CDS
( B ) LOCATION: 445..2445 (SEQ ID NO 3)

( i x ) FEATURE:
( A ) NAME/KEY: CDS
( B ) LOCATION: 976..2445 (SEQ ID NO 4)

( x i ) SEQUENCE DESCRIPTION: SEQ ID NO: 1:

| | | | | | | | | | | | | | | | | |
|---|---|---|---|---|---|---|---|---|---|---|---|---|---|---|---|---|
| GGC | GAT | GGC | TGT | AAG | ATC | CTC | CTG | GAC | ACC | AGC | CAG | ACC | TTT | GTG | AGA | 48 |
| Gly | Asp | Gly | Cys | Lys | Ile | Leu | Leu | Asp | Thr | Ser | Gln | Thr | Phe | Val | Arg | |
| 1 | | | | 5 | | | | | 10 | | | | | 15 | | |
| CAA | GGT | TCC | CTC | ATT | CAG | GTG | CCC | ATG | TCT | GAA | AAG | GGC | AAG | ATC | ACC | 96 |
| Gln | Gly | Ser | Leu | Ile | Gln | Val | Pro | Met | Ser | Glu | Lys | Gly | Lys | Ile | Thr | |
| | | | 20 | | | | | 25 | | | | | 30 | | | |
| AGG | GGG | CGC | CTG | GGG | TCT | CTC | TCC | CTA | AAG | AAA | GAG | GGC | GAG | CGA | CAG | 144 |
| Arg | Gly | Arg | Leu | Gly | Ser | Leu | Ser | Leu | Lys | Lys | Glu | Gly | Glu | Arg | Gln | |
| | | 35 | | | | | 40 | | | | | 45 | | | | |
| TGC | TTC | CTG | TTT | TCT | AAG | CAT | CTG | ATT | ATC | TGT | ACC | AGA | GGC | TCT | GGA | 192 |
| Cys | Phe | Leu | Phe | Ser | Lys | His | Leu | Ile | Ile | Cys | Thr | Arg | Gly | Ser | Gly | |
| | 50 | | | | | 55 | | | | | 60 | | | | | |
| GGG | AAG | CTT | CAC | TTG | ACC | AAG | AAT | GGA | GTC | ATA | TCC | CTC | ATT | GAC | TGC | 240 |
| Gly | Lys | Leu | His | Leu | Thr | Lys | Asn | Gly | Val | Ile | Ser | Leu | Ile | Asp | Cys | |
| 65 | | | | | 70 | | | | | 75 | | | | | 80 | |
| ACT | TTA | TTG | GAG | GAG | CCA | GAA | AGC | ACG | GAG | GAG | GAA | GCC | AAA | GGA | TCC | 288 |
| Thr | Leu | Leu | Glu | Glu | Pro | Glu | Ser | Thr | Glu | Glu | Glu | Ala | Lys | Gly | Ser | |
| | | | | 85 | | | | | 90 | | | | | 95 | | |
| GGC | CAA | GAC | ATA | GAT | CAC | TTG | GAT | TTT | AAA | ATC | GGG | GTG | GAG | CCA | AAG | 336 |
| Gly | Gln | Asp | Ile | Asp | His | Leu | Asp | Phe | Lys | Ile | Gly | Val | Glu | Pro | Lys | |
| | | | 100 | | | | | 105 | | | | | 110 | | | |
| GAT | TCC | CCG | CCC | TTT | ACA | GTC | ATC | CTA | GTG | GCC | TCG | TCC | AGA | CAG | GAG | 384 |
| Asp | Ser | Pro | Pro | Phe | Thr | Val | Ile | Leu | Val | Ala | Ser | Ser | Arg | Gln | Glu | |
| | | 115 | | | | | 120 | | | | | 125 | | | | |
| AAG | GCA | GCG | TGG | ACC | AGT | GAC | ATC | AGC | CAG | TGT | GTT | GGT | AAC | ATC | CGA | 432 |
| Lys | Ala | Ala | Trp | Thr | Ser | Asp | Ile | Ser | Gln | Cys | Val | Gly | Asn | Ile | Arg | |
| | 130 | | | | | 135 | | | | | 140 | | | | | |
| TGC | AAT | GGG | CTC | ATG | ATG | AAG | CCA | TTT | GAA | GAA | AAT | TCC | AAG | GTC | ACT | 480 |
| Cys | Asn | Gly | Leu | Met | Met | Lys | Pro | Phe | Glu | Glu | Asn | Ser | Lys | Val | Thr | |
| 145 | | | | | 150 | | | | | 155 | | | | | 160 | |
| GTG | CCG | CAG | ATG | ATC | AAG | TCC | GAC | GCC | TCC | TTA | TAT | TGT | GAT | GAT | GTT | 528 |
| Val | Pro | Gln | Met | Ile | Lys | Ser | Asp | Ala | Ser | Leu | Tyr | Cys | Asp | Asp | Val | |
| | | | | 165 | | | | | 170 | | | | | 175 | | |

```
GAC ATT CGC TTC AGC AAA ACC ATG AAC TCC TGC AAA GTG CTG CAG ATC       576
Asp Ile Arg Phe Ser Lys Thr Met Asn Ser Cys Lys Val Leu Gln Ile
        180             185                 190

GCC TAC GCC AGT GTG GAG CGG CTG CTG GAG AGG CTG ACG GAC CTG CGC       624
Ala Tyr Ala Ser Val Glu Arg Leu Leu Glu Arg Leu Thr Asp Leu Arg
            195                 200                 205

TTC CTG AGC ATC GAC TTC CTC AAC ACC TTC CTG CAC TCC TAC CGC GTC       672
Phe Leu Ser Ile Asp Phe Leu Asn Thr Phe Leu His Ser Tyr Arg Val
        210                 215                 220

TTC ACC ACC GCC ATC GTG GTC CTG GAC AAG CTC ATT ACC ATC TAC AAG       720
Phe Thr Thr Ala Ile Val Val Leu Asp Lys Leu Ile Thr Ile Tyr Lys
225                     230                 235                 240

AAG CCT ATC AGT GCC ATT CCT GCC AGG TCG CTG GAG CTC CTG TTT GCC       768
Lys Pro Ile Ser Ala Ile Pro Ala Arg Ser Leu Glu Leu Leu Phe Ala
                245                 250                 255

AGT GGC CAG AAC AAT AAG CTC CTG TAC GGT GAA CCC CCC AAG TCC CCG       816
Ser Gly Gln Asn Asn Lys Leu Leu Tyr Gly Glu Pro Pro Lys Ser Pro
            260                 265                 270

CGC GCC ACC CGC AAG TTC TCC TCG CCG CCA CCT CTG TCC ATC ACC AAG       864
Arg Ala Thr Arg Lys Phe Ser Ser Pro Pro Pro Leu Ser Ile Thr Lys
        275                 280                 285

ACA TCG TCA CCG AGC CGC CGG CGG AAG CTC TCC CTG AAC ATC CCC ATC       912
Thr Ser Ser Pro Ser Arg Arg Arg Lys Leu Ser Leu Asn Ile Pro Ile
    290                 295                 300

ATC ACT GGC GGC AAG GCC CTG GAC CTG GCC GCC CTC AGC TGC AAC TCC       960
Ile Thr Gly Gly Lys Ala Leu Asp Leu Ala Ala Leu Ser Cys Asn Ser
305                 310                 315                 320

AAT GGC TAC ACC AGC ATG TAC TCG GCC ATG TCA CCC TTC AGC AAG GCC      1008
Asn Gly Tyr Thr Ser Met Tyr Ser Ala Met Ser Pro Phe Ser Lys Ala
                325                 330                 335

ACG CTG GAC ACC AGC AAG CTC TAT GTG TCC AGC AGC TTC ACC AAC AAG      1056
Thr Leu Asp Thr Ser Lys Leu Tyr Val Ser Ser Ser Phe Thr Asn Lys
            340                 345                 350

ATT CCA GAT GAG GGC GAT ACG ACC CCT GAG AAG CCC GAA GAC CCT TCA      1104
Ile Pro Asp Glu Gly Asp Thr Thr Pro Glu Lys Pro Glu Asp Pro Ser
        355                 360                 365

GCG CTC AGC AAG CAG AGC TCA GAA GTC TCC ATG AGA GAG GAG TCA GAT      1152
Ala Leu Ser Lys Gln Ser Ser Glu Val Ser Met Arg Glu Glu Ser Asp
    370                 375                 380

ATT GAT CAA AAC CAG AGT GAT GAT GGT GAT ACT GAA ACA TCA CCA ACT      1200
Ile Asp Gln Asn Gln Ser Asp Asp Gly Asp Thr Glu Thr Ser Pro Thr
385                 390                 395                 400

AAA TCT CCA ACA ACA CCC AAA TCA GTC AAA AAC AAA AAT TCT TCA GAG      1248
Lys Ser Pro Thr Thr Pro Lys Ser Val Lys Asn Lys Asn Ser Ser Glu
                405                 410                 415

TTC CCA CTC TTT TCC TAT AAC AAT GGA GTC GTC ATG ACC TCC TGT CGT      1296
Phe Pro Leu Phe Ser Tyr Asn Asn Gly Val Val Met Thr Ser Cys Arg
            420                 425                 430

GAA CTG GAC AAT AAC CGC AGT GCC TTG TCG GCC GCC TCT GCC TTT GCC      1344
Glu Leu Asp Asn Asn Arg Ser Ala Leu Ser Ala Ala Ser Ala Phe Ala
        435                 440                 445

ATA GCA ACC GCC GGG GCC AAC GAG GGC ACC CCA AAC AAG GAG AAG TAC      1392
Ile Ala Thr Ala Gly Ala Asn Glu Gly Thr Pro Asn Lys Glu Lys Tyr
    450                 455                 460

CGG AGG ATG TCC TTA GCC AGT GCA GGG TTT CCC CCA GAC CAG AGG AAT      1440
Arg Arg Met Ser Leu Ala Ser Ala Gly Phe Pro Pro Asp Gln Arg Asn
465                 470                 475                 480

GGA GAC AAG GAG TTT GTG ATC CGC AGA GCA GCC ACC AAT CGT GTC TTG      1488
Gly Asp Lys Glu Phe Val Ile Arg Arg Ala Ala Thr Asn Arg Val Leu
                485                 490                 495
```

```
AAC GTG CTC CGC CAC TGG GTG TCC AAG CAC TCT CAG GAC TTT GAG ACC    1536
Asn Val Leu Arg His Trp Val Ser Lys His Ser Gln Asp Phe Glu Thr
            500             505             510

AAC GAT GAG CTC AAA TGC AAG GTG ATC GGC TTC CTG GAA GAA GTC ATG    1584
Asn Asp Glu Leu Lys Cys Lys Val Ile Gly Phe Leu Glu Glu Val Met
            515             520             525

CAC GAC CCG GAG CTC CTG ACC CAG GAG CGG AAG GCT GCA GCC AAC ATC    1632
His Asp Pro Glu Leu Leu Thr Gln Glu Arg Lys Ala Ala Ala Asn Ile
            530             535             540

ATC AGG ACT CTG ACC CAG GAG GAC CCA GGT GAC AAC CAG ATC ACG CTG    1680
Ile Arg Thr Leu Thr Gln Glu Asp Pro Gly Asp Asn Gln Ile Thr Leu
545             550             555             560

GAG GAG ATC ACG CAG ATG GCT GAA GGC GTG AAG GCT GAG CCC TTT GAA    1728
Glu Glu Ile Thr Gln Met Ala Glu Gly Val Lys Ala Glu Pro Phe Glu
            565             570             575

AAC CAC TCA GCC CTG GAG ATC GCG GAG CAG CTG ACC CTG CTA GAT CAC    1776
Asn His Ser Ala Leu Glu Ile Ala Glu Gln Leu Thr Leu Leu Asp His
            580             585             590

CTC GTC TTC AAG AAG ATT CCT TAT GAG GAG TTC TTC GGA CAA GGA TGG    1824
Leu Val Phe Lys Lys Ile Pro Tyr Glu Glu Phe Phe Gly Gln Gly Trp
            595             600             605

ATG AAA CTG GAA AAG AAT GAA AGG ACC CCT TAT ATC ATG AAA ACC ACT    1872
Met Lys Leu Glu Lys Asn Glu Arg Thr Pro Tyr Ile Met Lys Thr Thr
            610             615             620

AAG CAC TTC AAT GAC ATC AGT AAC TTG ATT GCT TCA GAA ATC ATC CGC    1920
Lys His Phe Asn Asp Ile Ser Asn Leu Ile Ala Ser Glu Ile Ile Arg
625             630             635             640

AAT GAG GAC ATC AAC GCC AGG GTG AGC GCC ATC GAG AAG TGG GTG GCC    1968
Asn Glu Asp Ile Asn Ala Arg Val Ser Ala Ile Glu Lys Trp Val Ala
            645             650             655

GTA GCT GAC ATA TGC CGC TGC CTC CAC AAC TAC AAT GCC GTA CTG GAG    2016
Val Ala Asp Ile Cys Arg Cys Leu His Asn Tyr Asn Ala Val Leu Glu
            660             665             670

ATC ACC TCG TCC ATG AAC CGC AGT GCA ATC TTC CGG CTC AAA AAG ACG    2064
Ile Thr Ser Ser Met Asn Arg Ser Ala Ile Phe Arg Leu Lys Lys Thr
            675             680             685

TGG CTC AAA GTC TCT AAG CAG ACT AAA GCT TTG ATT GAT AAG CTC CAA    2112
Trp Leu Lys Val Ser Lys Gln Thr Lys Ala Leu Ile Asp Lys Leu Gln
690             695             700

AAG CTT GTG TCA TCT GAG GGC AGA TTT AAG AAT CTC AGA GAA GCT TTG    2160
Lys Leu Val Ser Ser Glu Gly Arg Phe Lys Asn Leu Arg Glu Ala Leu
705             710             715             720

AAA AAT TGT GAC CCA CCC TGT GTC CCT TAC CTG GGG ATG TAC CTC ACC    2208
Lys Asn Cys Asp Pro Pro Cys Val Pro Tyr Leu Gly Met Tyr Leu Thr
            725             730             735

GAC CTG GCC TTC ATC GAG GAG GGG ACG CCC AAT TAC ACG GAA GAC GGC    2256
Asp Leu Ala Phe Ile Glu Glu Gly Thr Pro Asn Tyr Thr Glu Asp Gly
            740             745             750

CTG GTC AAC TTC TCC AAG ATG AGG ATG ATA TCC CAT ATT ATC CGA GAG    2304
Leu Val Asn Phe Ser Lys Met Arg Met Ile Ser His Ile Ile Arg Glu
            755             760             765

ATT CGC CAG TTT CAA CAA ACT GCC TAC AAA ATA GAG CAC CAA GCA AAG    2352
Ile Arg Gln Phe Gln Gln Thr Ala Tyr Lys Ile Glu His Gln Ala Lys
            770             775             780

GTA ACG CAA TAT TTA CTG GAC CAA TCT TTT GTA ATG GAT GAA GAA AGC    2400
Val Thr Gln Tyr Leu Leu Asp Gln Ser Phe Val Met Asp Glu Glu Ser
785             790             795             800

CTC TAC GAG TCT TCT CTC CGA ATA GAA CCA AAA CTC CCC ACC TGAAGCTGTG 2452
Leu Tyr Glu Ser Ser Leu Arg Ile Glu Pro Lys Leu Pro Thr
            805             810             815
```

```
CCCAGCCCAG ACCCAGCTGC TCCCGGGGAC ATGTGCTAGA TGATACTGTA CATATTCGTT    2512

TGGTTTCACT GGATTTTCTT CTTCAGTATG TGCTTCTCCA AGAATACAAA TCGTCCTTGT    2572

TCTTAGATTC CTGTAGAACC GGAATATGAA TTTCTGCACC GTTTCAGACT TCGCCCACCC    2632

ATCCCTCCCC TCGCCCGAAT                                                 2652
```

( 2 ) INFORMATION FOR SEQ ID NO: 2:

( i ) SEQUENCE CHARACTERISTICS:
        ( A ) LENGTH: 814 amino acids
        ( B ) TYPE: amino acid
        ( D ) TOPOLOGY: linear ( x i ) SEQUENCE DESCRIPTION: SEQ ID NO: 2:

```
Gly  Asp  Gly  Cys  Lys  Ile  Leu  Leu  Asp  Thr  Ser  Gln  Thr  Phe  Val  Arg
 1              5                        10                        15

Gln  Gly  Ser  Leu  Ile  Gln  Val  Pro  Met  Ser  Glu  Lys  Gly  Lys  Ile  Thr
               20                        25                        30

Arg  Gly  Arg  Leu  Gly  Ser  Leu  Ser  Leu  Lys  Lys  Glu  Gly  Glu  Arg  Gln
               35                        40                        45

Cys  Phe  Leu  Phe  Ser  Lys  His  Leu  Ile  Ile  Cys  Thr  Arg  Gly  Ser  Gly
      50                        55                        60

Gly  Lys  Leu  His  Leu  Thr  Lys  Asn  Gly  Val  Ile  Ser  Leu  Ile  Asp  Cys
 65                        70                        75                        80

Thr  Leu  Leu  Glu  Glu  Pro  Glu  Ser  Thr  Glu  Glu  Ala  Lys  Gly  Ser
                    85                        90                        95

Gly  Gln  Asp  Ile  Asp  His  Leu  Asp  Phe  Lys  Ile  Gly  Val  Glu  Pro  Lys
                    100                       105                       110

Asp  Ser  Pro  Pro  Phe  Thr  Val  Ile  Leu  Val  Ala  Ser  Ser  Arg  Gln  Glu
               115                       120                       125

Lys  Ala  Ala  Trp  Thr  Ser  Asp  Ile  Ser  Gln  Cys  Val  Gly  Asn  Ile  Arg
     130                       135                       140

Cys  Asn  Gly  Leu  Met  Met  Lys  Pro  Phe  Glu  Glu  Asn  Ser  Lys  Val  Thr
145                       150                       155                       160

Val  Pro  Gln  Met  Ile  Lys  Ser  Asp  Ala  Ser  Leu  Tyr  Cys  Asp  Asp  Val
                    165                       170                       175

Asp  Ile  Arg  Phe  Ser  Lys  Thr  Met  Asn  Ser  Cys  Lys  Val  Leu  Gln  Ile
                    180                       185                       190

Ala  Tyr  Ala  Ser  Val  Glu  Arg  Leu  Leu  Glu  Arg  Leu  Thr  Asp  Leu  Arg
               195                       200                       205

Phe  Leu  Ser  Ile  Asp  Phe  Leu  Asn  Thr  Phe  Leu  His  Ser  Tyr  Arg  Val
     210                       215                       220

Phe  Thr  Thr  Ala  Ile  Val  Val  Leu  Asp  Lys  Leu  Ile  Thr  Ile  Tyr  Lys
225                       230                       235                       240

Lys  Pro  Ile  Ser  Ala  Ile  Pro  Ala  Arg  Ser  Leu  Glu  Leu  Leu  Phe  Ala
                    245                       250                       255

Ser  Gly  Gln  Asn  Asn  Lys  Leu  Leu  Tyr  Gly  Glu  Pro  Pro  Lys  Ser  Pro
                    260                       265                       270

Arg  Ala  Thr  Arg  Lys  Phe  Ser  Ser  Pro  Pro  Leu  Ser  Ile  Thr  Lys
               275                       280                       285

Thr  Ser  Ser  Pro  Ser  Arg  Arg  Arg  Lys  Leu  Ser  Leu  Asn  Ile  Pro  Ile
     290                       295                       300

Ile  Thr  Gly  Gly  Lys  Ala  Leu  Asp  Leu  Ala  Ala  Leu  Ser  Cys  Asn  Ser
305                       310                       315                       320

Asn  Gly  Tyr  Thr  Ser  Met  Tyr  Ser  Ala  Met  Ser  Pro  Phe  Ser  Lys  Ala
                    325                       330                       335
```

```
Thr Leu Asp Thr Ser Lys Leu Tyr Val Ser Ser Ser Phe Thr Asn Lys
            340                 345                 350

Ile Pro Asp Glu Gly Asp Thr Thr Pro Glu Lys Pro Glu Asp Pro Ser
            355                 360                 365

Ala Leu Ser Lys Gln Ser Ser Glu Val Ser Met Arg Glu Glu Ser Asp
            370                 375                 380

Ile Asp Gln Asn Gln Ser Asp Asp Gly Asp Thr Glu Thr Ser Pro Thr
385                 390                 395                 400

Lys Ser Pro Thr Thr Pro Lys Ser Val Lys Asn Lys Asn Ser Ser Glu
            405                 410                 415

Phe Pro Leu Phe Ser Tyr Asn Asn Gly Val Val Met Thr Ser Cys Arg
            420                 425                 430

Glu Leu Asp Asn Asn Arg Ser Ala Leu Ser Ala Ala Ser Ala Phe Ala
            435                 440                 445

Ile Ala Thr Ala Gly Ala Asn Glu Gly Thr Pro Asn Lys Glu Lys Tyr
            450                 455                 460

Arg Arg Met Ser Leu Ala Ser Ala Gly Phe Pro Pro Asp Gln Arg Asn
465                 470                 475                 480

Gly Asp Lys Glu Phe Val Ile Arg Arg Ala Ala Thr Asn Arg Val Leu
            485                 490                 495

Asn Val Leu Arg His Trp Val Ser Lys His Ser Gln Asp Phe Glu Thr
            500                 505                 510

Asn Asp Glu Leu Lys Cys Lys Val Ile Gly Phe Leu Glu Glu Val Met
            515                 520                 525

His Asp Pro Glu Leu Leu Thr Gln Glu Arg Lys Ala Ala Ala Asn Ile
            530                 535                 540

Ile Arg Thr Leu Thr Gln Glu Asp Pro Gly Asp Asn Gln Ile Thr Leu
545                 550                 555                 560

Glu Glu Ile Thr Gln Met Ala Glu Gly Val Lys Ala Glu Pro Phe Glu
            565                 570                 575

Asn His Ser Ala Leu Glu Ile Ala Glu Gln Leu Thr Leu Leu Asp His
            580                 585                 590

Leu Val Phe Lys Lys Ile Pro Tyr Glu Glu Phe Phe Gly Gln Gly Trp
            595                 600                 605

Met Lys Leu Glu Lys Asn Glu Arg Thr Pro Tyr Ile Met Lys Thr Thr
            610                 615                 620

Lys His Phe Asn Asp Ile Ser Asn Leu Ile Ala Ser Glu Ile Ile Arg
625                 630                 635                 640

Asn Glu Asp Ile Asn Ala Arg Val Ser Ala Ile Glu Lys Trp Val Ala
            645                 650                 655

Val Ala Asp Ile Cys Arg Cys Leu His Asn Tyr Asn Ala Val Leu Glu
            660                 665                 670

Ile Thr Ser Ser Met Asn Arg Ser Ala Ile Phe Arg Leu Lys Lys Thr
            675                 680                 685

Trp Leu Lys Val Ser Lys Gln Thr Lys Ala Leu Ile Asp Lys Leu Gln
            690                 695                 700

Lys Leu Val Ser Ser Glu Gly Arg Phe Lys Asn Leu Arg Glu Ala Leu
705                 710                 715                 720

Lys Asn Cys Asp Pro Cys Val Pro Tyr Leu Gly Met Tyr Leu Thr
            725                 730                 735

Asp Leu Ala Phe Ile Glu Glu Gly Thr Pro Asn Tyr Thr Glu Asp Gly
            740                 745                 750

Leu Val Asn Phe Ser Lys Met Arg Met Ile Ser His Ile Ile Arg Glu
```

```
                     755                          760                           765
Ile Arg Gln Phe Gln Gln Thr Ala Tyr Lys Ile Glu His Gln Ala Lys
    770                     775                 780

Val Thr Gln Tyr Leu Leu Asp Gln Ser Phe Val Met Asp Glu Glu Ser
785                     790                 795                         800

Leu Tyr Glu Ser Ser Leu Arg Ile Glu Pro Lys Leu Pro Thr
                805                     810
```

( 2 ) INFORMATION FOR SEQ ID NO: 3:

( i ) SEQUENCE CHARACTERISTICS:
        ( A ) LENGTH: 666 amino acids
        ( B ) TYPE: amino acid
        ( D ) TOPOLOGY: linear ( x i ) SEQUENCE DESCRIPTION: SEQ ID NO: 3:

```
Met Met Lys Pro Phe Glu Glu Asn Ser Lys Val Thr Val Pro Gln Met
  1             5                  10                  15

Ile Lys Ser Asp Ala Ser Leu Tyr Cys Asp Asp Val Asp Ile Arg Phe
            20                  25                  30

Ser Lys Thr Met Asn Ser Cys Lys Val Leu Gln Ile Ala Tyr Ala Ser
        35                  40                  45

Val Glu Arg Leu Leu Glu Arg Leu Thr Asp Leu Arg Phe Leu Ser Ile
 50                  55                  60

Asp Phe Leu Asn Thr Phe Leu His Ser Tyr Arg Val Phe Thr Thr Ala
 65                  70                  75                      80

Ile Val Val Leu Asp Lys Leu Ile Thr Ile Tyr Lys Lys Pro Ile Ser
                 85                  90                  95

Ala Ile Pro Ala Arg Ser Leu Glu Leu Leu Phe Ala Ser Gly Gln Asn
            100                 105                 110

Asn Lys Leu Leu Tyr Gly Glu Pro Pro Lys Ser Pro Arg Ala Thr Arg
            115                 120                 125

Lys Phe Ser Ser Pro Pro Leu Ser Ile Thr Lys Thr Ser Ser Pro
    130                 135                 140

Ser Arg Arg Arg Lys Leu Ser Leu Asn Ile Pro Ile Ile Thr Gly Gly
145                 150                 155                 160

Lys Ala Leu Asp Leu Ala Ala Leu Ser Cys Asn Ser Asn Gly Tyr Thr
                165                 170                 175

Ser Met Tyr Ser Ala Met Ser Pro Phe Ser Lys Ala Thr Leu Asp Thr
            180                 185                 190

Ser Lys Leu Tyr Val Ser Ser Ser Phe Thr Asn Lys Ile Pro Asp Glu
            195                 200                 205

Gly Asp Thr Thr Pro Glu Lys Pro Glu Asp Pro Ser Ala Leu Ser Lys
            210                 215                 220

Gln Ser Ser Glu Val Ser Met Arg Glu Glu Ser Asp Ile Asp Gln Asn
225                 230                 235                 240

Gln Ser Asp Asp Gly Asp Thr Glu Thr Ser Pro Thr Lys Ser Pro Thr
                245                 250                 255

Thr Pro Lys Ser Val Lys Asn Lys Asn Ser Ser Glu Phe Pro Leu Phe
            260                 265                 270

Ser Tyr Asn Asn Gly Val Val Met Thr Ser Cys Arg Glu Leu Asp Asn
            275                 280                 285

Asn Arg Ser Ala Leu Ser Ala Ala Ser Ala Phe Ala Ile Ala Thr Ala
            290                 295                 300

Gly Ala Asn Glu Gly Thr Pro Asn Lys Glu Lys Tyr Arg Arg Met Ser
305                 310                 315                 320
```

| Leu | Ala | Ser | Ala | Gly | Phe | Pro | Pro | Asp | Gln | Arg | Asn | Gly | Asp | Lys | Glu |
|---|---|---|---|---|---|---|---|---|---|---|---|---|---|---|---|
| | | | | 325 | | | | 330 | | | | | | 335 | |

| Phe | Val | Ile | Arg | Arg | Ala | Ala | Thr | Asn | Arg | Val | Leu | Asn | Val | Leu | Arg |
|---|---|---|---|---|---|---|---|---|---|---|---|---|---|---|---|
| | | | 340 | | | | 345 | | | | | 350 | | | |

| His | Trp | Val | Ser | Lys | His | Ser | Gln | Asp | Phe | Glu | Thr | Asn | Asp | Glu | Leu |
|---|---|---|---|---|---|---|---|---|---|---|---|---|---|---|---|
| | | 355 | | | | | 360 | | | | | 365 | | | |

| Lys | Cys | Lys | Val | Ile | Gly | Phe | Leu | Glu | Glu | Val | Met | His | Asp | Pro | Glu |
|---|---|---|---|---|---|---|---|---|---|---|---|---|---|---|---|
| | 370 | | | | | 375 | | | | | 380 | | | | |

| Leu | Leu | Thr | Gln | Glu | Arg | Lys | Ala | Ala | Ala | Asn | Ile | Ile | Arg | Thr | Leu |
|---|---|---|---|---|---|---|---|---|---|---|---|---|---|---|---|
| 385 | | | | | 390 | | | | 395 | | | | | | 400 |

| Thr | Gln | Glu | Asp | Pro | Gly | Asp | Asn | Gln | Ile | Thr | Leu | Glu | Glu | Ile | Thr |
|---|---|---|---|---|---|---|---|---|---|---|---|---|---|---|---|
| | | | | 405 | | | | | 410 | | | | | 415 | |

| Gln | Met | Ala | Glu | Gly | Val | Lys | Ala | Glu | Pro | Phe | Glu | Asn | His | Ser | Ala |
|---|---|---|---|---|---|---|---|---|---|---|---|---|---|---|---|
| | | | 420 | | | | | 425 | | | | | 430 | | |

| Leu | Glu | Ile | Ala | Glu | Gln | Leu | Thr | Leu | Leu | Asp | His | Leu | Val | Phe | Lys |
|---|---|---|---|---|---|---|---|---|---|---|---|---|---|---|---|
| | | | 435 | | | | 440 | | | | | 445 | | | |

| Lys | Ile | Pro | Tyr | Glu | Glu | Phe | Gly | Gln | Gly | Trp | Met | Lys | Leu | Glu |
|---|---|---|---|---|---|---|---|---|---|---|---|---|---|---|
| | 450 | | | | | 455 | | | | 460 | | | | |

| Lys | Asn | Glu | Arg | Thr | Pro | Tyr | Ile | Met | Lys | Thr | Thr | Lys | His | Phe | Asn |
|---|---|---|---|---|---|---|---|---|---|---|---|---|---|---|---|
| 465 | | | | | 470 | | | | | 475 | | | | | 480 |

| Asp | Ile | Ser | Asn | Leu | Ile | Ala | Ser | Glu | Ile | Ile | Arg | Asn | Glu | Asp | Ile |
|---|---|---|---|---|---|---|---|---|---|---|---|---|---|---|---|
| | | | | 485 | | | | | 490 | | | | | 495 | |

| Asn | Ala | Arg | Val | Ser | Ala | Ile | Glu | Lys | Trp | Val | Ala | Val | Ala | Asp | Ile |
|---|---|---|---|---|---|---|---|---|---|---|---|---|---|---|---|
| | | | 500 | | | | | 505 | | | | | 510 | | |

| Cys | Arg | Cys | Leu | His | Asn | Tyr | Asn | Ala | Val | Leu | Glu | Ile | Thr | Ser | Ser |
|---|---|---|---|---|---|---|---|---|---|---|---|---|---|---|---|
| | | 515 | | | | | 520 | | | | | 525 | | | |

| Met | Asn | Arg | Ser | Ala | Ile | Phe | Arg | Leu | Lys | Lys | Thr | Trp | Leu | Lys | Val |
|---|---|---|---|---|---|---|---|---|---|---|---|---|---|---|---|
| | 530 | | | | | 535 | | | | | 540 | | | | |

| Ser | Lys | Gln | Thr | Lys | Ala | Leu | Ile | Asp | Lys | Leu | Gln | Lys | Leu | Val | Ser |
|---|---|---|---|---|---|---|---|---|---|---|---|---|---|---|---|
| 545 | | | | | 550 | | | | 555 | | | | | | 560 |

| Ser | Glu | Gly | Arg | Phe | Lys | Asn | Leu | Arg | Glu | Ala | Leu | Lys | Asn | Cys | Asp |
|---|---|---|---|---|---|---|---|---|---|---|---|---|---|---|---|
| | | | | 565 | | | | | 570 | | | | | 575 | |

| Pro | Pro | Cys | Val | Pro | Tyr | Leu | Gly | Met | Tyr | Leu | Thr | Asp | Leu | Ala | Phe |
|---|---|---|---|---|---|---|---|---|---|---|---|---|---|---|---|
| | | | 580 | | | | | 585 | | | | | 590 | | |

| Ile | Glu | Glu | Gly | Thr | Pro | Asn | Tyr | Thr | Glu | Asp | Gly | Leu | Val | Asn | Phe |
|---|---|---|---|---|---|---|---|---|---|---|---|---|---|---|---|
| | | 595 | | | | | 600 | | | | | 605 | | | |

| Ser | Lys | Met | Arg | Met | Ile | Ser | His | Ile | Ile | Arg | Glu | Ile | Arg | Gln | Phe |
|---|---|---|---|---|---|---|---|---|---|---|---|---|---|---|---|
| | 610 | | | | | 615 | | | | | 620 | | | | |

| Gln | Gln | Thr | Ala | Tyr | Lys | Ile | Glu | His | Gln | Ala | Lys | Val | Thr | Gln | Tyr |
|---|---|---|---|---|---|---|---|---|---|---|---|---|---|---|---|
| 625 | | | | | 630 | | | | | 635 | | | | | 640 |

| Leu | Leu | Asp | Gln | Ser | Phe | Val | Met | Asp | Glu | Glu | Ser | Leu | Tyr | Glu | Ser |
|---|---|---|---|---|---|---|---|---|---|---|---|---|---|---|---|
| | | | | 645 | | | | | 650 | | | | | 655 | |

| Ser | Leu | Arg | Ile | Glu | Pro | Lys | Leu | Pro | Thr |
|---|---|---|---|---|---|---|---|---|---|
| | | | 660 | | | | | 665 | |

(2) INFORMATION FOR SEQ ID NO: 4:

(i) SEQUENCE CHARACTERISTICS:
        (A) LENGTH: 489 amino acids
        (B) TYPE: amino acid
        (D) TOPOLOGY: linear (xi) SEQUENCE DESCRIPTION: SEQ ID NO: 4:

| Met | Tyr | Ser | Ala | Met | Ser | Pro | Phe | Ser | Lys | Ala | Thr | Leu | Asp | Thr | Ser |
|---|---|---|---|---|---|---|---|---|---|---|---|---|---|---|---|
| 1 | | | | 5 | | | | | 10 | | | | | 15 | |

| | | | | | | | | | | | | | | |
|---|---|---|---|---|---|---|---|---|---|---|---|---|---|---|
| Lys | Leu | Tyr | Val 20 | Ser | Ser | Ser | Phe | Thr | Asn 25 | Lys | Ile | Pro | Asp 30 | Glu | Gly |
| Asp | Thr | Thr 35 | Pro | Glu | Lys | Pro | Glu 40 | Asp | Pro | Ser | Ala | Leu 45 | Ser | Lys | Gln |
| Ser | Ser 50 | Glu | Val | Ser | Met | Arg 55 | Glu | Glu | Ser | Asp | Ile 60 | Asp | Gln | Asn | Gln |
| Ser 65 | Asp | Asp | Gly | Asp | Thr 70 | Glu | Thr | Ser | Pro | Thr 75 | Lys | Ser | Pro | Thr | Thr 80 |
| Pro | Lys | Ser | Val | Lys 85 | Asn | Lys | Asn | Ser | Ser 90 | Glu | Phe | Pro | Leu | Phe 95 | Ser |
| Tyr | Asn | Asn | Gly 100 | Val | Val | Met | Thr | Ser 105 | Cys | Arg | Glu | Leu | Asp 110 | Asn | Asn |
| Arg | Ser | Ala 115 | Leu | Ser | Ala | Ala | Ser 120 | Ala | Phe | Ala | Ile | Ala 125 | Thr | Ala | Gly |
| Ala | Asn 130 | Glu | Gly | Thr | Pro | Asn 135 | Lys | Glu | Lys | Tyr | Arg 140 | Arg | Met | Ser | Leu |
| Ala 145 | Ser | Ala | Gly | Phe | Pro 150 | Pro | Asp | Gln | Arg | Asn 155 | Gly | Asp | Lys | Glu | Phe 160 |
| Val | Ile | Arg | Arg | Ala 165 | Ala | Thr | Asn | Arg | Val 170 | Leu | Asn | Val | Leu | Arg 175 | His |
| Trp | Val | Ser | Lys 180 | His | Ser | Gln | Asp | Phe 185 | Glu | Thr | Asn | Asp | Glu 190 | Leu | Lys |
| Cys | Lys | Val 195 | Ile | Gly | Phe | Leu | Glu 200 | Glu | Val | Met | His | Asp 205 | Pro | Glu | Leu |
| Leu | Thr 210 | Gln | Glu | Arg | Lys | Ala 215 | Ala | Ala | Asn | Ile | Ile 220 | Arg | Thr | Leu | Thr |
| Gln 225 | Glu | Asp | Pro | Gly | Asp 230 | Asn | Gln | Ile | Thr | Leu 235 | Glu | Glu | Ile | Thr | Gln 240 |
| Met | Ala | Glu | Gly | Val 245 | Lys | Ala | Glu | Pro | Phe 250 | Glu | Asn | His | Ser | Ala 255 | Leu |
| Glu | Ile | Ala | Glu 260 | Gln | Leu | Thr | Leu | Leu 265 | Asp | His | Leu | Val | Phe 270 | Lys | Lys |
| Ile | Pro | Tyr 275 | Glu | Glu | Phe | Phe | Gly 280 | Gln | Gly | Trp | Met | Lys 285 | Leu | Glu | Lys |
| Asn | Glu 290 | Arg | Thr | Pro | Tyr | Ile 295 | Met | Lys | Thr | Thr | Lys 300 | His | Phe | Asn | Asp |
| Ile 305 | Ser | Asn | Leu | Ile | Ala 310 | Ser | Glu | Ile | Ile | Arg 315 | Asn | Glu | Asp | Ile | Asn 320 |
| Ala | Arg | Val | Ser | Ala 325 | Ile | Glu | Lys | Trp | Val 330 | Ala | Val | Ala | Asp | Ile 335 | Cys |
| Arg | Cys | Leu | His 340 | Asn | Tyr | Asn | Ala | Val 345 | Leu | Glu | Ile | Thr | Ser 350 | Ser | Met |
| Asn | Arg | Ser 355 | Ala | Ile | Phe | Arg | Leu 360 | Lys | Lys | Thr | Trp | Leu 365 | Lys | Val | Ser |
| Lys | Gln 370 | Thr | Lys | Ala | Leu | Ile 375 | Asp | Lys | Leu | Gln | Lys 380 | Leu | Val | Ser | Ser |
| Glu 385 | Gly | Arg | Phe | Lys | Asn 390 | Leu | Arg | Glu | Ala | Leu 395 | Lys | Asn | Cys | Asp | Pro 400 |
| Pro | Cys | Val | Pro | Tyr 405 | Leu | Gly | Met | Tyr | Leu 410 | Thr | Asp | Leu | Ala | Phe 415 | Ile |
| Glu | Glu | Gly | Thr 420 | Pro | Asn | Tyr | Thr | Glu 425 | Asp | Gly | Leu | Val | Asn 430 | Phe | Ser |
| Lys | Met | Arg 435 | Met | Ile | Ser | His | Ile 440 | Ile | Arg | Glu | Ile | Arg 445 | Gln | Phe | Gln |

| | | | | | | | | | | | | | | |
|---|---|---|---|---|---|---|---|---|---|---|---|---|---|---|
| Gln | Thr | Ala | Tyr | Lys | Ile | Glu | His | Gln | Ala | Lys | Val | Thr | Gln | Tyr | Leu |
| | 450 | | | | 455 | | | | 460 | | | | | | |
| Leu | Asp | Gln | Ser | Phe | Val | Met | Asp | Glu | Glu | Ser | Leu | Tyr | Glu | Ser | Ser |
| 465 | | | | | 470 | | | | 475 | | | | | | 480 |
| Leu | Arg | Ile | Glu | Pro | Lys | Leu | Pro | Thr | | | | | | | |
| | | | | 485 | | | | | | | | | | | |

(2) INFORMATION FOR SEQ ID NO: 5:

(i) SEQUENCE CHARACTERISTICS:
        (A) LENGTH: 1092 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iii) ANTI-SENSE: NO (ix) FEATURE:
        (A) NAME/KEY: CDS
        (B) LOCATION: 1..1092

(xi) SEQUENCE DESCRIPTION: SEQ ID NO: 5:

| | | | | | | | | | | | | | | | |
|---|---|---|---|---|---|---|---|---|---|---|---|---|---|---|---|
| ATT | ACT | AAA | ATA | ATC | CAA | AGG | AAA | AAA | ATT | GCA | AGA | GAC | AAT | GGA | CCA | 48 |
| Ile | Thr | Lys | Ile | Ile | Gln | Arg | Lys | Lys | Ile | Ala | Arg | Asp | Asn | Gly | Pro | |
| 1 | | | | 5 | | | | | 10 | | | | | 15 | | |
| GGT | CAT | AAT | ATT | ACA | TTT | CAG | AGT | TCA | CCT | CCC | ACA | GTT | GAG | TGG | CAT | 96 |
| Gly | His | Asn | Ile | Thr | Phe | Gln | Ser | Ser | Pro | Pro | Thr | Val | Glu | Trp | His | |
| | | | 20 | | | | 25 | | | | 30 | | | | | |
| ATA | AGC | AGA | CCT | GGG | CAC | ATA | GAG | ACT | TTT | GAC | CTG | CTC | ACC | TTA | CAC | 144 |
| Ile | Ser | Arg | Pro | Gly | His | Ile | Glu | Thr | Phe | Asp | Leu | Leu | Thr | Leu | His | |
| | | 35 | | | | 40 | | | | 45 | | | | | | |
| CCA | ATA | GAA | ATT | GCT | CGA | CAA | CTC | ACT | TTA | CTT | GAT | TCA | GAT | CTA | TAC | 192 |
| Pro | Ile | Glu | Ile | Ala | Arg | Gln | Leu | Thr | Leu | Leu | Asp | Ser | Asp | Leu | Tyr | |
| | 50 | | | | 55 | | | | 60 | | | | | | | |
| CGA | GCT | GTA | CAG | CCA | TCA | GAT | TTA | GTT | GGA | AGT | GTG | TGG | ACA | AAA | GAA | 240 |
| Arg | Ala | Val | Gln | Pro | Ser | Asp | Leu | Val | Gly | Ser | Val | Trp | Thr | Lys | Glu | |
| 65 | | | | | 70 | | | | | 75 | | | | | 80 | |
| GAC | AAA | GAA | ATT | AAC | TCT | CCT | AAT | CTT | CTG | AAA | ATG | ATT | CGA | CAT | ACC | 288 |
| Asp | Lys | Glu | Ile | Asn | Ser | Pro | Asn | Leu | Leu | Lys | Met | Ile | Arg | His | Thr | |
| | | | | 85 | | | | | 90 | | | | | 95 | | |
| ACC | AAC | CTC | ACT | CTG | TGG | TTT | GAG | AAA | TGT | ATT | GTA | GAA | ACT | GAA | AAT | 336 |
| Thr | Asn | Leu | Thr | Leu | Trp | Phe | Glu | Lys | Cys | Ile | Val | Glu | Thr | Glu | Asn | |
| | | | 100 | | | | 105 | | | | 110 | | | | | |
| TTA | GAA | GAA | AGA | GTA | GCT | GTG | GTG | AGT | CGA | ATT | ATT | GAG | ATT | CTA | CAA | 384 |
| Leu | Glu | Glu | Arg | Val | Ala | Val | Val | Ser | Arg | Ile | Ile | Glu | Ile | Leu | Gln | |
| | | 115 | | | | 120 | | | | 125 | | | | | | |
| GTC | TTT | CAA | GAG | TTG | AAC | AAC | TTT | AAT | GGG | GTC | CTT | GAG | GTT | GTC | AGT | 432 |
| Val | Phe | Gln | Glu | Leu | Asn | Asn | Phe | Asn | Gly | Val | Leu | Glu | Val | Val | Ser | |
| | 130 | | | | 135 | | | | 140 | | | | | | | |
| GCT | ATG | AAT | TCC | TCA | CCT | GTT | TAC | AGA | CTA | GAC | CAC | ACA | TTT | GAG | CAA | 480 |
| Ala | Met | Asn | Ser | Ser | Pro | Val | Tyr | Arg | Leu | Asp | His | Thr | Phe | Glu | Gln | |
| 145 | | | | | 150 | | | | 155 | | | | | | 160 | |
| ATA | CCA | AGT | CGC | CAG | AAG | AAA | ATT | TTA | GAA | GAA | GCT | CAT | GAA | TTG | AGT | 528 |
| Ile | Pro | Ser | Arg | Gln | Lys | Lys | Ile | Leu | Glu | Glu | Ala | His | Glu | Leu | Ser | |
| | | | | 165 | | | | | 170 | | | | | 175 | | |
| GAA | GAT | CAC | TAT | AAG | AAA | TAT | TTG | GCA | AAA | CTC | AGG | TCT | ATT | AAT | CCA | 576 |
| Glu | Asp | His | Tyr | Lys | Lys | Tyr | Leu | Ala | Lys | Leu | Arg | Ser | Ile | Asn | Pro | |
| | | | 180 | | | | 185 | | | | 190 | | | | | |
| CCA | TGT | GTG | CCT | TTC | TTT | GGA | ATT | TAT | CTA | CAT | AAT | ATC | TTG | AAA | ACA | 624 |

|  |  |  |  |  |  |  |  |  |  |  |  |  |  |  |  |
|---|---|---|---|---|---|---|---|---|---|---|---|---|---|---|---|
| Pro | Cys<br>195 | Val | Pro | Phe | Phe | Gly | Ile<br>200 | Tyr | Leu | His | Asn<br>205 | Ile | Leu | Lys | Thr |
| GAA<br>Glu<br>210 | AAA<br>Glu | GGC<br>Gly | AAC<br>Asn | CCT<br>Pro | GAG<br>Glu | GTC<br>Val<br>215 | CTA<br>Leu | AAA<br>Lys | AGA<br>Arg | CAT<br>His | GGA<br>Gly<br>220 | AAA<br>Lys | GAG<br>Glu | CTT<br>Leu | ATA<br>Ile | 672 |
| AAC<br>Asn<br>225 | TTT<br>Phe | AGC<br>Ser | AAA<br>Lys | AGG<br>Arg | AGG<br>Arg<br>230 | AAA<br>Lys | GTA<br>Val | GCA<br>Ala | GAA<br>Glu | ATA<br>Ile<br>235 | ACA<br>Thr | GGA<br>Gly | GAG<br>Glu | ATC<br>Ile | CAG<br>Gln<br>240 | 720 |
| CAG<br>Gln | TAC<br>Tyr | CAA<br>Gln | AAT<br>Asn | CAG<br>Gln<br>245 | CCT<br>Pro | TAC<br>Tyr | TGT<br>Cys | TTA<br>Leu | CGA<br>Arg<br>250 | GTA<br>Val | GAA<br>Glu | TCA<br>Ser | GAT<br>Asp | ATC<br>Ile<br>255 | AAA<br>Lys | 768 |
| AGG<br>Arg | TTC<br>Phe | TTT<br>Phe | GAA<br>Glu<br>260 | AAC<br>Asn | TTG<br>Leu | AAT<br>Asn | CCG<br>Pro | ATG<br>Met<br>265 | GGA<br>Gly | AAT<br>Asn | AGC<br>Ser | ATG<br>Met | GAG<br>Glu<br>270 | AGG<br>Arg | GAA<br>Glu | 816 |
| TTT<br>Phe | ACA<br>Thr | GAT<br>Asp<br>275 | TAT<br>Tyr | CTT<br>Leu | TTC<br>Phe | AAC<br>Asn | AAA<br>Lys<br>280 | TCC<br>Ser | CTA<br>Leu | GAA<br>Glu | ATA<br>Ile | GAA<br>Glu<br>285 | CCA<br>Pro | CGA<br>Arg | AAC<br>Asn | 864 |
| CCT<br>Pro | AAG<br>Lys<br>290 | CCT<br>Pro | CTC<br>Leu | CCA<br>Pro | AGA<br>Arg | TTT<br>Phe<br>295 | CCA<br>Pro | AAA<br>Lys | AAA<br>Lys | TAT<br>Tyr | ACG<br>Thr<br>300 | TAT<br>Tyr | CCC<br>Pro | CTA<br>Leu | AAA<br>Lys | 912 |
| TCT<br>Ser<br>305 | CCT<br>Pro | GGT<br>Gly | GTC<br>Val | CGG<br>Arg | CCA<br>Pro<br>310 | TCA<br>Ser | AAC<br>Asn | CCA<br>Pro | AGA<br>Arg | CCG<br>Pro<br>315 | GGT<br>Gly | ACC<br>Thr | ATG<br>Met | AGG<br>Arg | ATC<br>Ile<br>320 | 960 |
| CCC<br>Pro | ACC<br>Thr | CCT<br>Pro | CTA<br>Leu | CAG<br>Gln<br>325 | CAG<br>Gln | GAA<br>Glu | CCA<br>Pro | CGA<br>Arg | AAA<br>Lys<br>330 | ATA<br>Ile | AGT<br>Ser | TAT<br>Tyr | AGT<br>Ser | AGA<br>Arg<br>335 | ATA<br>Ile | 1008 |
| CCA<br>Pro | GAG<br>Glu | TCA<br>Ser | GAG<br>Glu<br>340 | ACA<br>Thr | GAG<br>Glu | AGT<br>Ser | ACT<br>Thr | GCT<br>Ala<br>345 | AGT<br>Ser | GCA<br>Ala | CCT<br>Pro | AAT<br>Asn | TCA<br>Ser<br>350 | CCA<br>Pro | AGG<br>Arg | 1056 |
| ACA<br>Thr | CCT<br>Pro | CTA<br>Leu<br>355 | ACA<br>Thr | CCT<br>Pro | CCA<br>Pro | CCT<br>Pro | GCA<br>Ala<br>360 | TCA<br>Ser | GGA<br>Gly | ACA<br>Thr | TCA<br>Ser |  |  |  |  | 1092 |

( 2 ) INFORMATION FOR SEQ ID NO: 6:

( i ) SEQUENCE CHARACTERISTICS:
        ( A ) LENGTH: 364 amino acids
        ( B ) TYPE: amino acid
        ( D ) TOPOLOGY: linear ( x i ) SEQUENCE DESCRIPTION: SEQ ID NO: 6:

|  |  |  |  |  |  |  |  |  |  |  |  |  |  |  |
|---|---|---|---|---|---|---|---|---|---|---|---|---|---|---|
| Ile<br>1 | Thr | Lys | Ile | Ile<br>5 | Gln | Arg | Lys | Lys | Ile<br>10 | Ala | Arg | Asp | Asn | Gly<br>15 | Pro |
| Gly | His | Asn | Ile<br>20 | Thr | Phe | Gln | Ser | Ser<br>25 | Pro | Pro | Thr | Val | Glu<br>30 | Trp | His |
| Ile | Ser | Arg<br>35 | Pro | Gly | His | Ile | Glu<br>40 | Thr | Phe | Asp | Leu | Leu<br>45 | Thr | Leu | His |
| Pro | Ile<br>50 | Glu | Ile | Ala | Arg | Gln<br>55 | Leu | Thr | Leu | Leu | Asp<br>60 | Ser | Asp | Leu | Tyr |
| Arg<br>65 | Ala | Val | Gln | Pro | Ser<br>70 | Asp | Leu | Val | Gly | Ser<br>75 | Val | Trp | Thr | Lys | Glu<br>80 |
| Asp | Lys | Glu | Ile | Asn<br>85 | Ser | Pro | Asn | Leu | Leu<br>90 | Lys | Met | Ile | Arg | His<br>95 | Thr |
| Thr | Asn | Leu | Thr<br>100 | Leu | Trp | Phe | Glu | Lys<br>105 | Cys | Ile | Val | Glu | Thr<br>110 | Glu | Asn |
| Leu | Glu | Glu<br>115 | Arg | Val | Ala | Val | Val<br>120 | Ser | Arg | Ile | Ile | Glu<br>125 | Ile | Leu | Gln |
| Val | Phe<br>130 | Gln | Glu | Leu | Asn | Asn<br>135 | Phe | Asn | Gly | Val | Leu<br>140 | Glu | Val | Val | Ser |

```
Ala  Met  Asn  Ser  Ser  Pro  Val  Tyr  Arg  Leu  Asp  His  Thr  Phe  Glu  Gln
145            150                      155                      160

Ile  Pro  Ser  Arg  Gln  Lys  Lys  Ile  Leu  Glu  Glu  Ala  His  Glu  Leu  Ser
                    165                      170                      175

Glu  Asp  His  Tyr  Lys  Lys  Tyr  Leu  Ala  Lys  Leu  Arg  Ser  Ile  Asn  Pro
               180                      185                      190

Pro  Cys  Val  Pro  Phe  Phe  Gly  Ile  Tyr  Leu  His  Asn  Ile  Leu  Lys  Thr
          195                      200                      205

Glu  Glu  Gly  Asn  Pro  Glu  Val  Leu  Lys  Arg  His  Gly  Lys  Glu  Leu  Ile
     210                      215                      220

Asn  Phe  Ser  Lys  Arg  Arg  Lys  Val  Ala  Glu  Ile  Thr  Gly  Glu  Ile  Gln
225                      230                      235                      240

Gln  Tyr  Gln  Asn  Gln  Pro  Tyr  Cys  Leu  Arg  Val  Glu  Ser  Asp  Ile  Lys
                    245                      250                      255

Arg  Phe  Phe  Glu  Asn  Leu  Asn  Pro  Met  Gly  Asn  Ser  Met  Glu  Arg  Glu
               260                      265                      270

Phe  Thr  Asp  Tyr  Leu  Phe  Asn  Lys  Ser  Leu  Glu  Ile  Glu  Pro  Arg  Asn
          275                      280                      285

Pro  Lys  Pro  Leu  Pro  Arg  Phe  Pro  Lys  Lys  Tyr  Thr  Tyr  Pro  Leu  Lys
     290                      295                      300

Ser  Pro  Gly  Val  Arg  Pro  Ser  Asn  Pro  Arg  Pro  Gly  Thr  Met  Arg  Ile
305                      310                      315                      320

Pro  Thr  Pro  Leu  Gln  Gln  Glu  Pro  Arg  Lys  Ile  Ser  Tyr  Ser  Arg  Ile
                    325                      330                      335

Pro  Glu  Ser  Glu  Thr  Glu  Ser  Thr  Ala  Ser  Ala  Pro  Asn  Ser  Pro  Arg
               340                      345                      350

Thr  Pro  Leu  Thr  Pro  Pro  Pro  Ala  Ser  Gly  Thr  Ser
          355                      360
```

( 2 ) INFORMATION FOR SEQ ID NO: 7:

( i ) SEQUENCE CHARACTERISTICS:
        ( A ) LENGTH: 1956 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i i i ) ANTI-SENSE: NO ( i x ) FEATURE:
        ( A ) NAME/KEY: CDS
        ( B ) LOCATION: 1..1956

( x i ) SEQUENCE DESCRIPTION: SEQ ID NO: 7:

```
AGG  TTT  GAA  ATC  CCA  GAG  CCA  GAA  CCT  ACA  GAA  GCA  GAT  AAA  CTA  GCA       48
Arg  Phe  Glu  Ile  Pro  Glu  Pro  Glu  Pro  Thr  Glu  Ala  Asp  Lys  Leu  Ala
 1                   5                        10                       15

CTT  GAG  AAA  GGA  GAA  CAA  CCA  ATC  TCT  GCA  GAT  CTA  AAG  AGG  TTC  AGA       96
Leu  Glu  Lys  Gly  Glu  Gln  Pro  Ile  Ser  Ala  Asp  Leu  Lys  Arg  Phe  Arg
              20                       25                       30

AAG  GAA  TAT  ATC  CAA  CCA  GTA  CAG  CTA  CGG  GTG  TTG  AAC  GTG  CAG  CGG      144
Lys  Glu  Tyr  Ile  Gln  Pro  Val  Gln  Leu  Arg  Val  Leu  Asn  Val  Gln  Arg
         35                       40                       45

CAC  TGG  GTT  GAA  CAT  CAC  CCC  CAT  GAC  TTT  GAA  AGA  GAC  TTG  GAA  CTG      192
His  Trp  Val  Glu  His  His  Pro  His  Asp  Phe  Glu  Arg  Asp  Leu  Glu  Leu
    50                       55                       60

CTC  GAA  AGA  CTA  GAA  TCC  TTC  ACC  TCA  AGC  GCT  CAC  AGA  GCG  AAA  GCA      240
```

| | | | | | | | | | | | | | | | | |
|---|---|---|---|---|---|---|---|---|---|---|---|---|---|---|---|---|
| Leu | Glu | Arg | Leu | Glu | Ser | Phe | Thr | Ser | Ser | Ala | His | Arg | Ala | Lys | Ala | |
| 65 | | | | 70 | | | | | 75 | | | | | 80 | | |
| ATG | AAG | AAG | TGG | GTA | GAG | AGC | ATC | GCT | AAG | ACC | ATC | AGG | AGG | AAG | AAG | 288 |
| Met | Lys | Lys | Trp | Val | Glu | Ser | Ile | Ala | Lys | Thr | Ile | Arg | Arg | Lys | Lys | |
| | | | | 85 | | | | | 90 | | | | | 95 | | |
| CAA | GCT | CAG | GCA | AAT | GGA | GTA | AGC | CAT | AAT | ATT | ACC | TTT | GAA | AGT | CCA | 336 |
| Gln | Ala | Gln | Ala | Asn | Gly | Val | Ser | His | Asn | Ile | Thr | Phe | Glu | Ser | Pro | |
| | | | | 100 | | | | | 105 | | | | | 110 | | |
| CCT | CCA | CCA | ATT | GAA | TGG | CAT | ATC | AGC | AAA | CCA | GGA | CAG | TTT | GAA | ACA | 384 |
| Pro | Pro | Pro | Ile | Glu | Trp | His | Ile | Ser | Lys | Pro | Gly | Gln | Phe | Glu | Thr | |
| | | 115 | | | | | 120 | | | | | 125 | | | | |
| TTT | GAT | CTC | ATG | ACA | CTT | CAT | CCA | ATA | GAA | ATT | GCA | CGT | CAG | CTG | ACA | 432 |
| Phe | Asp | Leu | Met | Thr | Leu | His | Pro | Ile | Glu | Ile | Ala | Arg | Gln | Leu | Thr | |
| | 130 | | | | | 135 | | | | | 140 | | | | | |
| CTT | TTG | GAG | TCT | GAT | CTT | TAC | AGG | AAA | GTT | CAA | CCG | TCT | GAA | CTT | GTA | 480 |
| Leu | Leu | Glu | Ser | Asp | Leu | Tyr | Arg | Lys | Val | Gln | Pro | Ser | Glu | Leu | Val | |
| 145 | | | | | 150 | | | | | 155 | | | | | 160 | |
| GGG | AGT | GTG | TGG | ACC | AAA | GAA | GAT | AAA | GAA | ATA | AAT | TCT | CCA | AAT | TTA | 528 |
| Gly | Ser | Val | Trp | Thr | Lys | Glu | Asp | Lys | Glu | Ile | Asn | Ser | Pro | Asn | Leu | |
| | | | | 165 | | | | | 170 | | | | | 175 | | |
| TTA | AAA | ATG | ATT | CGC | CAT | ACC | ACA | AAT | CTC | ACC | CTC | TGG | TTT | GAA | AAA | 576 |
| Leu | Lys | Met | Ile | Arg | His | Thr | Thr | Asn | Leu | Thr | Leu | Trp | Phe | Glu | Lys | |
| | | | 180 | | | | | 185 | | | | | 190 | | | |
| TGC | ATT | GTG | GAA | GCA | GAA | AAT | TTT | GAA | GAA | CGG | GTG | GCA | GTA | CTA | AGT | 624 |
| Cys | Ile | Val | Glu | Ala | Glu | Asn | Phe | Glu | Glu | Arg | Val | Ala | Val | Leu | Ser | |
| | | 195 | | | | | 200 | | | | | 205 | | | | |
| AGA | ATT | ATA | GAA | ATT | CTG | CAA | GTT | TTT | CGA | GAT | TTG | AAT | AAT | TTC | AAT | 672 |
| Arg | Ile | Ile | Glu | Ile | Leu | Gln | Val | Phe | Arg | Asp | Leu | Asn | Asn | Phe | Asn | |
| 210 | | | | | 215 | | | | | 220 | | | | | | |
| GGC | GTA | TTG | GAG | ATA | GTC | AGT | GCA | GTA | AAT | TCA | GTG | TCA | GTA | TAC | AGA | 720 |
| Gly | Val | Leu | Glu | Ile | Val | Ser | Ala | Val | Asn | Ser | Val | Ser | Val | Tyr | Arg | |
| 225 | | | | | 230 | | | | | 235 | | | | | 240 | |
| CTA | GAC | CAT | ACC | TTT | GAG | GCA | CTG | CAG | GAA | AGG | AAA | AGG | AAA | ATT | TTG | 768 |
| Leu | Asp | His | Thr | Phe | Glu | Ala | Leu | Gln | Glu | Arg | Lys | Arg | Lys | Ile | Leu | |
| | | | | 245 | | | | | 250 | | | | | 255 | | |
| GAC | GAA | GCT | GTG | GAA | TTA | AGT | CAA | GAT | CAC | TTT | AAA | AAA | TAC | CTA | GTA | 816 |
| Asp | Glu | Ala | Val | Glu | Leu | Ser | Gln | Asp | His | Phe | Lys | Lys | Tyr | Leu | Val | |
| | | | | 260 | | | | | 265 | | | | | 270 | | |
| AAA | CTT | AAG | TCA | ATC | AAT | CCA | CCT | TGT | GTG | CCT | TTT | TTT | GGA | ATA | TAT | 864 |
| Lys | Leu | Lys | Ser | Ile | Asn | Pro | Pro | Cys | Val | Pro | Phe | Phe | Gly | Ile | Tyr | |
| | | 275 | | | | | 280 | | | | | 285 | | | | |
| TTA | ACA | AAT | ATT | CTG | AAG | ACC | GAA | GAA | GGG | AAT | AAT | GAT | TTT | TTA | AAA | 912 |
| Leu | Thr | Asn | Ile | Leu | Lys | Thr | Glu | Glu | Gly | Asn | Asn | Asp | Phe | Leu | Lys | |
| 290 | | | | | 295 | | | | | 300 | | | | | | |
| AAG | AAA | GGG | AAA | GAT | TTA | ATC | AAT | TTC | AGT | AAG | AGG | AGG | AAA | GTA | GCT | 960 |
| Lys | Lys | Gly | Lys | Asp | Leu | Ile | Asn | Phe | Ser | Lys | Arg | Arg | Lys | Val | Ala | |
| 305 | | | | | 310 | | | | | 315 | | | | | 320 | |
| GAA | ATT | ACT | GGA | GAA | ATT | CAG | CAG | TAT | CAG | AAT | CAG | CCG | TAC | TGC | CTA | 1008 |
| Glu | Ile | Thr | Gly | Glu | Ile | Gln | Gln | Tyr | Gln | Asn | Gln | Pro | Tyr | Cys | Leu | |
| | | | | 325 | | | | | 330 | | | | | 335 | | |
| CGG | ATA | GAA | CCA | GAT | ATG | AGG | AGA | TTC | TTT | GAA | AAC | CTT | AAC | CCC | ATG | 1056 |
| Arg | Ile | Glu | Pro | Asp | Met | Arg | Arg | Phe | Phe | Glu | Asn | Leu | Asn | Pro | Met | |
| | | | 340 | | | | | 345 | | | | | 350 | | | |
| GGA | AGT | GCA | TGT | GAA | AAA | GAG | TTT | ACA | GAT | TAT | TTG | TTC | AAC | AAA | AGT | 1104 |
| Gly | Ser | Ala | Cys | Glu | Lys | Glu | Phe | Thr | Asp | Tyr | Leu | Phe | Asn | Lys | Ser | |
| | | 355 | | | | | 360 | | | | | 365 | | | | |
| TTA | GAA | ATA | GAA | CCA | CGA | AAT | TGT | AAA | CAG | CCA | CCA | CGA | TTT | CCA | CGA | 1152 |
| Leu | Glu | Ile | Glu | Pro | Arg | Asn | Cys | Lys | Gln | Pro | Pro | Arg | Phe | Pro | Arg | |
| | | | | 370 | | | | | 375 | | | | | 380 | | |
| AAA | AGT | ACA | TTT | GAA | CTA | AAA | GAA | CCA | GGA | ATA | CGA | CCA | AAT | GCA | GGA | 1200 |

-continued

| | | | | | | | | | | | | | | | |
|---|---|---|---|---|---|---|---|---|---|---|---|---|---|---|---|
| Lys 385 | Ser | Thr | Phe | Glu 390 | Leu | Lys | Glu | Pro | Gly 395 | Ile | Arg | Pro | Asn | Ala | Gly 400 |

| CGA | CAT | GGA | GAA | ACA | AGT | GGA | ACA | AGA | GGA | CAT | CCA | ACA | CCT | CTA | GAA | 1248 |
|---|---|---|---|---|---|---|---|---|---|---|---|---|---|---|---|---|
| Arg | His | Gly | Glu | Thr 405 | Ser | Gly | Thr | Arg | Gly 410 | His | Pro | Thr | Pro | Leu 415 | Glu | |

| AGA | GAA | CCA | TAT | AAA | ATA | GAA | TTT | GAA | AGA | ATA | GCT | GAA | ACA | GAA | CTA | 1296 |
|---|---|---|---|---|---|---|---|---|---|---|---|---|---|---|---|---|
| Arg | Glu | Pro | Tyr 420 | Lys | Ile | Glu | Phe | Glu 425 | Arg | Ile | Ala | Glu | Thr 430 | Glu | Leu | |

| GAA | AGT | ACA | GTA | AGT | GCA | CCA | ACA | AGT | CCA | AAT | ACT | CCC | TCA | ACA | CCA | 1344 |
|---|---|---|---|---|---|---|---|---|---|---|---|---|---|---|---|---|
| Glu | Ser | Thr 435 | Val | Ser | Ala | Pro | Thr 440 | Ser | Pro | Asn | Thr | Pro 445 | Ser | Thr | Pro | |

| CCA | GTT | TCA | GCA | TCA | TCA | GAT | CAC | TCA | GTA | TTT | TTA | GAT | GTA | GAT | CTA | 1392 |
|---|---|---|---|---|---|---|---|---|---|---|---|---|---|---|---|---|
| Pro | Val 450 | Ser | Ala | Ser | Ser | Asp 455 | His | Ser | Val | Phe | Leu 460 | Asp | Val | Asp | Leu | |

| AAC | AGT | AGT | CAC | GGA | TCA | AAC | ACA | ATC | TTT | GCA | CCT | GTG | CTA | CTA | CCA | 1440 |
|---|---|---|---|---|---|---|---|---|---|---|---|---|---|---|---|---|
| Asn 465 | Ser | Ser | His | Gly | Ser 470 | Asn | Thr | Ile | Phe | Ala 475 | Pro | Val | Leu | Leu | Pro 480 | |

| AAG | TCC | AAG | TCT | TTC | TTT | AGT | TCA | TGT | GGA | AGT | TTA | CAT | AAA | CTA | AGT | 1488 |
|---|---|---|---|---|---|---|---|---|---|---|---|---|---|---|---|---|
| Lys | Ser | Lys | Ser | Phe 485 | Phe | Ser | Ser | Cys | Gly 490 | Ser | Leu | His | Lys | Leu 495 | Ser | |

| GAA | GAG | CCC | CTG | ATT | CCT | CCT | CCT | CTT | CCT | CCT | CGA | AAA | AAG | TTT | GAT | 1536 |
|---|---|---|---|---|---|---|---|---|---|---|---|---|---|---|---|---|
| Glu | Glu | Pro | Leu 500 | Ile | Pro | Pro | Pro | Leu 505 | Pro | Pro | Arg | Lys | Lys 510 | Phe | Asp | |

| CAT | GAT | GGC | TCA | AAT | TCC | AAG | GGA | AAT | ATG | AAA | TCT | GAT | GAT | GAT | CCT | 1584 |
|---|---|---|---|---|---|---|---|---|---|---|---|---|---|---|---|---|
| His | Asp | Gly 515 | Ser | Asn | Ser | Lys | Gly 520 | Asn | Met | Lys | Ser | Asp 525 | Asp | Asp | Pro | |

| CCT | GCT | ATT | CCA | CCG | AGA | CAG | CCT | CCT | CCT | CCA | AAG | GTA | AAA | CCC | AGA | 1632 |
|---|---|---|---|---|---|---|---|---|---|---|---|---|---|---|---|---|
| Pro | Ala 530 | Ile | Pro | Pro | Arg | Gln 535 | Pro | Pro | Pro | Pro | Lys 540 | Val | Lys | Pro | Arg | |

| GTT | CCT | GTT | CCT | ACT | GGT | GCA | TTT | GAT | GGG | CCT | CTG | CAT | AGT | CCA | CCT | 1680 |
|---|---|---|---|---|---|---|---|---|---|---|---|---|---|---|---|---|
| Val 545 | Pro | Val | Pro | Thr | Gly 550 | Ala | Phe | Asp | Gly | Pro 555 | Leu | His | Ser | Pro | Pro 560 | |

| CCG | CCA | CCA | CCA | AGA | GAT | CCT | CTT | CCT | GAT | ACC | CCT | CCA | CCA | GTT | CCC | 1728 |
|---|---|---|---|---|---|---|---|---|---|---|---|---|---|---|---|---|
| Pro | Pro | Pro | Pro | Arg 565 | Asp | Pro | Leu | Pro | Asp 570 | Thr | Pro | Pro | Pro | Val 575 | Pro | |

| CTT | CGG | CCT | CCA | GAA | CAC | TTT | ATA | AAC | TGT | CCA | TTT | AAT | CTT | CAG | CCA | 1776 |
|---|---|---|---|---|---|---|---|---|---|---|---|---|---|---|---|---|
| Leu | Arg | Pro | Pro 580 | Glu | His | Phe | Ile | Asn 585 | Cys | Pro | Phe | Asn | Leu 590 | Gln | Pro | |

| CCT | CCA | CTG | GGG | CAT | CTT | CAC | AGA | GAT | TCA | GAC | TGG | CTC | AGA | GAC | ATT | 1824 |
|---|---|---|---|---|---|---|---|---|---|---|---|---|---|---|---|---|
| Pro | Pro | Leu 595 | Gly | His | Leu | His 600 | Arg | Asp | Ser | Asp | Trp 605 | Leu | Arg | Asp | Ile | |

| AGT | ACG | TGT | CCA | AAT | TCG | CCA | AGC | ACT | CCT | CCT | AGC | ACA | CCC | TCT | CCA | 1872 |
|---|---|---|---|---|---|---|---|---|---|---|---|---|---|---|---|---|
| Ser | Thr 610 | Cys | Pro | Asn | Ser | Pro 615 | Ser | Thr | Pro | Pro | Ser 620 | Thr | Pro | Ser | Pro | |

| AGG | GTA | CCG | CGT | CGA | TGC | TAT | GTG | CTC | AGT | TCT | AGT | CAG | AAT | AAT | CTT | 1920 |
|---|---|---|---|---|---|---|---|---|---|---|---|---|---|---|---|---|
| Arg 625 | Val | Pro | Arg | Arg | Cys 630 | Tyr | Val | Leu | Ser | Ser 635 | Ser | Gln | Asn | Asn | Leu 640 | |

| GCT | CAT | CCT | CCA | GCT | CCC | CCT | GTT | CCA | CCA | AGG | GAG | | | | | 1956 |
|---|---|---|---|---|---|---|---|---|---|---|---|---|---|---|---|---|
| Ala | His | Pro | Pro | Ala 645 | Pro | Pro | Val | Pro | Pro 650 | Arg | Glu | | | | | |

( 2 ) INFORMATION FOR SEQ ID NO: 8:

( i ) SEQUENCE CHARACTERISTICS:
        ( A ) LENGTH: 652 amino acids
        ( B ) TYPE: amino acid
        ( D ) TOPOLOGY: linear ( x i ) SEQUENCE DESCRIPTION: SEQ ID NO: 8:

| Arg | Phe | Glu | Ile | Pro | Glu | Pro | Glu | Pro | Thr | Glu | Ala | Asp | Lys | Leu | Ala |
|---|---|---|---|---|---|---|---|---|---|---|---|---|---|---|---|
| 1 | | | | 5 | | | | | 10 | | | | | 15 | |

| | | | | | | | | | | | | | | |
|---|---|---|---|---|---|---|---|---|---|---|---|---|---|---|
| Leu | Glu | Lys | Gly | Glu | Gln | Pro | Ile | Ser | Ala | Asp | Leu | Lys | Arg | Phe | Arg |
| | | | 20 | | | | | 25 | | | | 30 | | |
| Lys | Glu | Tyr | Ile | Gln | Pro | Val | Gln | Leu | Arg | Val | Leu | Asn | Val | Gln | Arg |
| | | | 35 | | | | 40 | | | | | 45 | | | |
| His | Trp | Val | Glu | His | His | Pro | His | Asp | Phe | Glu | Arg | Asp | Leu | Glu | Leu |
| | | 50 | | | | | 55 | | | | | 60 | | | |
| Leu | Glu | Arg | Leu | Glu | Ser | Phe | Thr | Ser | Ser | Ala | His | Arg | Ala | Lys | Ala |
| 65 | | | | | 70 | | | | | 75 | | | | | 80 |
| Met | Lys | Lys | Trp | Val | Glu | Ser | Ile | Ala | Lys | Thr | Ile | Arg | Arg | Lys | Lys |
| | | | | 85 | | | | | 90 | | | | | 95 | |
| Gln | Ala | Gln | Ala | Asn | Gly | Val | Ser | His | Asn | Ile | Thr | Phe | Glu | Ser | Pro |
| | | | | 100 | | | | | 105 | | | | 110 | | |
| Pro | Pro | Pro | Ile | Glu | Trp | His | Ile | Ser | Lys | Pro | Gly | Gln | Phe | Glu | Thr |
| | | 115 | | | | | 120 | | | | | 125 | | | |
| Phe | Asp | Leu | Met | Thr | Leu | His | Pro | Ile | Glu | Ile | Ala | Arg | Gln | Leu | Thr |
| | 130 | | | | | 135 | | | | | 140 | | | | |
| Leu | Leu | Glu | Ser | Asp | Leu | Tyr | Arg | Lys | Val | Gln | Pro | Ser | Glu | Leu | Val |
| 145 | | | | | 150 | | | | | 155 | | | | | 160 |
| Gly | Ser | Val | Trp | Thr | Lys | Glu | Asp | Lys | Glu | Ile | Asn | Ser | Pro | Asn | Leu |
| | | | | 165 | | | | | 170 | | | | | 175 | |
| Leu | Lys | Met | Ile | Arg | His | Thr | Thr | Asn | Leu | Thr | Leu | Trp | Phe | Glu | Lys |
| | | | 180 | | | | | 185 | | | | | 190 | | |
| Cys | Ile | Val | Glu | Ala | Glu | Asn | Phe | Glu | Glu | Arg | Val | Ala | Val | Leu | Ser |
| | | | 195 | | | | | 200 | | | | 205 | | | |
| Arg | Ile | Ile | Glu | Ile | Leu | Gln | Val | Phe | Arg | Asp | Leu | Asn | Asn | Phe | Asn |
| | 210 | | | | | 215 | | | | | 220 | | | | |
| Gly | Val | Leu | Glu | Ile | Val | Ser | Ala | Val | Asn | Ser | Val | Ser | Val | Tyr | Arg |
| 225 | | | | | 230 | | | | | 235 | | | | | 240 |
| Leu | Asp | His | Thr | Phe | Glu | Ala | Leu | Gln | Glu | Arg | Lys | Arg | Lys | Ile | Leu |
| | | | | 245 | | | | | 250 | | | | | 255 | |
| Asp | Glu | Ala | Val | Glu | Leu | Ser | Gln | Asp | His | Phe | Lys | Lys | Tyr | Leu | Val |
| | | | 260 | | | | | 265 | | | | | 270 | | |
| Lys | Leu | Lys | Ser | Ile | Asn | Pro | Pro | Cys | Val | Pro | Phe | Phe | Gly | Ile | Tyr |
| | | 275 | | | | | 280 | | | | | 285 | | | |
| Leu | Thr | Asn | Ile | Leu | Lys | Thr | Glu | Glu | Gly | Asn | Asn | Asp | Phe | Leu | Lys |
| | 290 | | | | | 295 | | | | | 300 | | | | |
| Lys | Lys | Gly | Lys | Asp | Leu | Ile | Asn | Phe | Ser | Lys | Arg | Arg | Lys | Val | Ala |
| 305 | | | | | 310 | | | | | 315 | | | | | 320 |
| Glu | Ile | Thr | Gly | Glu | Ile | Gln | Gln | Tyr | Gln | Asn | Gln | Pro | Tyr | Cys | Leu |
| | | | | 325 | | | | | 330 | | | | | 335 | |
| Arg | Ile | Glu | Pro | Asp | Met | Arg | Arg | Phe | Phe | Glu | Asn | Leu | Asn | Pro | Met |
| | | | | 340 | | | | | 345 | | | | | 350 | |
| Gly | Ser | Ala | Cys | Glu | Lys | Glu | Phe | Thr | Asp | Tyr | Leu | Phe | Asn | Lys | Ser |
| | | | 355 | | | | | 360 | | | | | 365 | | |
| Leu | Glu | Ile | Glu | Pro | Arg | Asn | Cys | Lys | Gln | Pro | Pro | Arg | Phe | Pro | Arg |
| | | 370 | | | | | 375 | | | | | 380 | | | |
| Lys | Ser | Thr | Phe | Glu | Leu | Lys | Glu | Pro | Gly | Ile | Arg | Pro | Asn | Ala | Gly |
| 385 | | | | | 390 | | | | | 395 | | | | | 400 |
| Arg | His | Gly | Glu | Thr | Ser | Gly | Thr | Arg | Gly | His | Pro | Thr | Pro | Leu | Glu |
| | | | | 405 | | | | | 410 | | | | | 415 | |
| Arg | Glu | Pro | Tyr | Lys | Ile | Glu | Phe | Glu | Arg | Ile | Ala | Glu | Thr | Glu | Leu |
| | | | 420 | | | | | 425 | | | | | 430 | | |
| Glu | Ser | Thr | Val | Ser | Ala | Pro | Thr | Ser | Pro | Asn | Thr | Pro | Ser | Thr | Pro |
| | | 435 | | | | | 440 | | | | | 445 | | | |

| | | | | | | | | | | | | | |
|---|---|---|---|---|---|---|---|---|---|---|---|---|---|
|Pro|Val 450|Ser|Ala|Ser|Ser|Asp 455|His|Ser|Val|Phe 460|Leu|Asp|Val|Asp|Leu|

| | | | | | | | | | | | | | |
|---|---|---|---|---|---|---|---|---|---|---|---|---|---|
|Asn 465|Ser|Ser|His|Gly|Ser 470|Asn|Thr|Ile|Phe|Ala 475|Pro|Val|Leu|Leu|Pro 480|

| | | | | | | | | | | | | | |
|---|---|---|---|---|---|---|---|---|---|---|---|---|---|
|Lys|Ser|Lys|Ser|Phe 485|Phe|Ser|Ser|Cys|Gly 490|Ser|Leu|His|Lys|Leu 495|Ser|

| | | | | | | | | | | | | | |
|---|---|---|---|---|---|---|---|---|---|---|---|---|---|
|Glu|Glu|Pro|Leu 500|Ile|Pro|Pro|Pro|Leu 505|Pro|Pro|Arg|Lys|Lys 510|Phe|Asp|

| | | | | | | | | | | | | | |
|---|---|---|---|---|---|---|---|---|---|---|---|---|---|
|His|Asp|Gly 515|Ser|Asn|Ser|Lys|Gly 520|Asn|Met|Lys|Ser|Asp 525|Asp|Pro|

| | | | | | | | | | | | | | |
|---|---|---|---|---|---|---|---|---|---|---|---|---|---|
|Pro|Ala 530|Ile|Pro|Pro|Arg|Gln 535|Pro|Pro|Pro|Lys 540|Val|Lys|Pro|Arg|

| | | | | | | | | | | | | | |
|---|---|---|---|---|---|---|---|---|---|---|---|---|---|
|Val 545|Pro|Val|Pro|Thr|Gly 550|Ala|Phe|Asp|Gly|Pro 555|Leu|His|Ser|Pro|Pro 560|

| | | | | | | | | | | | | | |
|---|---|---|---|---|---|---|---|---|---|---|---|---|---|
|Pro|Pro|Pro|Pro|Arg 565|Asp|Pro|Leu|Pro|Asp 570|Thr|Pro|Pro|Pro|Val 575|Pro|

| | | | | | | | | | | | | | |
|---|---|---|---|---|---|---|---|---|---|---|---|---|---|
|Leu|Arg|Pro|Pro 580|Glu|His|Phe|Ile|Asn 585|Cys|Pro|Phe|Asn|Leu 590|Gln|Pro|

| | | | | | | | | | | | | | |
|---|---|---|---|---|---|---|---|---|---|---|---|---|---|
|Pro|Pro|Leu 595|Gly|His|Leu|His|Arg 600|Asp|Ser|Asp|Trp|Leu 605|Arg|Asp|Ile|

| | | | | | | | | | | | | | |
|---|---|---|---|---|---|---|---|---|---|---|---|---|---|
|Ser|Thr 610|Cys|Pro|Asn|Ser|Pro 615|Ser|Thr|Pro|Pro|Ser 620|Thr|Pro|Ser|Pro|

| | | | | | | | | | | | | | |
|---|---|---|---|---|---|---|---|---|---|---|---|---|---|
|Arg 625|Val|Pro|Arg|Arg|Cys 630|Tyr|Val|Leu|Ser|Ser 635|Ser|Gln|Asn|Asn|Leu 640|

| | | | | | | | | |
|---|---|---|---|---|---|---|---|---|
|Ala|His|Pro|Pro|Ala 645|Pro|Pro|Val|Pro|Pro 650|Arg|Glu|

(2) INFORMATION FOR SEQ ID NO:9:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (ix) FEATURE:
        (A) NAME/KEY: modified_base
        (B) LOCATION: 15
        (D) OTHER INFORMATION: /mod_base=i (ix) FEATURE:
        (A) NAME/KEY: modified_base
        (B) LOCATION: 18
        (D) OTHER INFORMATION: /mod_base=i (ix) FEATURE:
        (A) NAME/KEY: modified_base
        (B) LOCATION: 21
        (D) OTHER INFORMATION: /mod_base=i (ix) FEATURE:
        (A) NAME/KEY: modified_base
        (B) LOCATION: 27
        (D) OTHER INFORMATION: /mod_base=i (ix) FEATURE:
        (A) NAME/KEY: modified_base
        (B) LOCATION: 30
        (D) OTHER INFORMATION: /mod_base=i ( i x ) FEATURE:
    ( A ) NAME/KEY: modified_base
    ( B ) LOCATION: 33
    ( D ) OTHER INFORMATION: /mod_base=i ( x i ) SEQUENCE DESCRIPTION: SEQ ID NO:9:

GATATCGAAT TCCGNGTN Y T NAA Y GTN Y-
TN MGNCA Y TGGG T                                                            4 1

( 2 ) INFORMATION FOR SEQ ID NO:10:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL: NO ( i v ) ANTI-SENSE: NO ( i x ) FEATURE:
        ( A ) NAME/KEY: modified_base
        ( B ) LOCATION: 15
        ( D ) OTHER INFORMATION: /mod_base=i ( i x ) FEATURE:
        ( A ) NAME/KEY: modified_base
        ( B ) LOCATION: 21
        ( D ) OTHER INFORMATION: /mod_base=i ( i x ) FEATURE:
        ( A ) NAME/KEY: modified_base
        ( B ) LOCATION: 30
        ( D ) OTHER INFORMATION: /mod_base=i ( i x ) FEATURE:
        ( A ) NAME/KEY: modified_base
        ( B ) LOCATION: 33
        ( D ) OTHER INFORMATION: /mod_base=i ( x i ) SEQUENCE DESCRIPTION: SEQ ID NO:10:

AAGCTTGAAT TCCKNMK Y TT NSWRAARTTN AKNA                                    3 4

( 2 ) INFORMATION FOR SEQ ID NO: 11:

( i ) SEQUENCE CHARACTERISTICS:
        ( A ) LENGTH: 33 bases
        ( B ) TYPE: nucleic acid
        ( C ) STRANDEDNESS: simple
        ( D ) TOPOLOGY: linear ( i i ) MOLECULE TYPE: other nucleic acid ( i i i ) HYPOTHETICAL: NO ( i i i ) ANTI-SENSE: NO ( x i ) SEQUENCE DESCRIPTION: SEQ ID NO: 11:

ATCHGTNAGG TACATNCCHA GGTAKGGNAC ACA                                            3 3

( 2 ) INFORMATION FOR SEQ ID NO: 12:

( i ) SEQUENCE CHARACTERISTICS:
        ( A ) LENGTH: 27 bases
        ( B ) TYPE: nucleic acid
        ( C ) STRANDEDNESS: simple
        ( D ) TOPOLOGY: linear ( i i ) MOLECULE TYPE: other nucleic acid ( x i ) SEQUENCE DESCRIPTION: SEQ ID NO: 12:

GCNATHTT Y C  GNCTNAARAA  RACNTGG                                                      27

We claim:

1. An isolated peptide selected from the group consisting of:
   (a) SEQ ID no. 2, 3, and 4, and
   (b) fragments of (a),
   wherein said peptide is capable of stimulating the levels of exchange of GDP with p21-GDP complexes.

2. An isolated nucleic acid encoding a peptide according to claim 1.

3. A nucleic acid according to claim 2, having a sequence selected from the group consisting of:
   (a) all or part of nucleotide 1-2442 of SEQ ID no. 1, and
   (b) sequences derived from (a) as a result of the degeneracy of the genetic code.

4. A method or preparing a peptide comprising culturing a cell containing a nucleic acid according to claim 2 under conditions for expression of said sequence, and recovering the produced peptide.

5. A composition comprising a nucleic acid according to claim 2 and a pharmaceutically acceptable carrier.

6. A vector comprising the nucleic acid of claim 2.

7. An isolated comprising the nucleic acid of claim 2.

8. A nucleic acid according to claim 2 having the sequence of SEQ ID no. 1.

9. A composition comprising a peptide according to claim 1 and a pharmaceutically acceptable carrier.

* * * * *

UNITED STATES PATENT AND TRADEMARK OFFICE
CERTIFICATE OF CORRECTION

PATENT NO. : 5,656,595
DATED : August 12, 1997
INVENTOR(S) : Fabien Schweighoffer, et al.

It is certified that error appears in the above—identified patent and that said Letters Patent is hereby corrected as shown below:

Please add the following word in Claim 7 in Column 44 after "An isolated":

--cell--

Signed and Sealed this

Twenty-eighth Day of October, 1997

Attest:

BRUCE LEHMAN

Attesting Officer     Commissioner of Patents and Trademarks